(12) United States Patent
Coleman et al.

(10) Patent No.: US 8,481,691 B2
(45) Date of Patent: Jul. 9, 2013

(54) METHOD FOR SELECTIVELY EXTRACTING MEMBRANE PROTEINS USING CALIXARENES

(75) Inventors: Anthony W. Coleman, Calluire (FR); Cyrille Mbemba, Lyons (FR); Pierre Falson, Annonay (FR); Rima Matar, Lyons (FR); Frederic Huche, La Ferte-Alais (FR)

(73) Assignees: Centre National de la Recherche Scientifique—CNRS, Paris (FR); Universite Claude Bernard de Lyon 1, Villeurbanne (FR)

( * ) Notice: Subject to any disclaimer, the term of this patent is extended or adjusted under 35 U.S.C. 154(b) by 116 days.

(21) Appl. No.: 12/994,417

(22) PCT Filed: May 28, 2009

(86) PCT No.: PCT/FR2009/000626
§ 371 (c)(1),
(2), (4) Date: Feb. 15, 2011

(87) PCT Pub. No.: WO2009/144419
PCT Pub. Date: Dec. 3, 2009

(65) Prior Publication Data
US 2011/0144314 A1 Jun. 16, 2011

(30) Foreign Application Priority Data
May 28, 2008 (FR) ...................................... 08 02894

(51) Int. Cl.
*C07K 1/14* (2006.01)
*B82Y 5/00* (2011.01)
(52) U.S. Cl.
USPC ........... 530/395; 530/350; 977/773; 977/797; 977/962
(58) Field of Classification Search
USPC .................. 530/395, 350; 977/773, 797, 962
See application file for complete search history.

(56) References Cited

FOREIGN PATENT DOCUMENTS
EP 0 954 965 A1 11/1999
WO WO 89/08092 A1 9/1989

OTHER PUBLICATIONS

T. Oshima, et al. "Selective Extraction and Recovery of Cytochrome c by Liquid-Liquid Extraction Using a Calix[6]arene Carboxylic Acid Derivative", Langmuir, vol. 21, Jun. 30, 2005, pp. 7280-7284 (XP002502667).
M. Martinez-Aragon, et al. "Host-guest extraction of munoglobulin G using calyx[6]arenas" Separation and Purification Technology, Mar. 26, 2008 (XP002502668).
M. Goto, et al. "Recent Advances in Protein Extraction and Chiral Separation of Biomolecules" Tsinghua Science and Technology, vol. 11, No. 2, Apr. 2006, pp. 194-201, Tsinghua University Press, Beijing CN, "2. Novel Liquid Membrane System for Chiral Separation" pp. 199-201 (XP005350941).

*Primary Examiner* — Chih-Min Kam
(74) *Attorney, Agent, or Firm* — Arent Fox LLP

(57) ABSTRACT

The present invention relates to a method for selectively extracting membrane proteins using at least one calixarene of formula (I). The use of calixarenes in the method according to the invention enables the selective solubilization of the membrane proteins while preserving the three-dimensional structure that is essential to the enzymatic activity thereof.

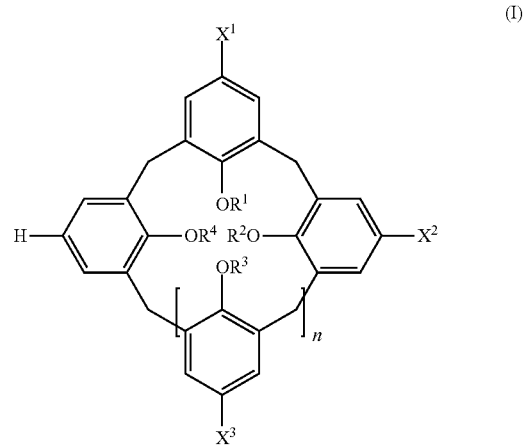

12 Claims, 14 Drawing Sheets

A

B

METHOD FOR SELECTIVELY EXTRACTING MEMBRANE PROTEINS USING CALIXARENES

CROSS-REFERENCE TO RELATED APPLICATION

This is a National Stage entry of International Application No. PCT/FR2009/000626, filed May 28, 2009, which claims priority from French Application No. 0802894, filed May 28, 2008. The disclosures of the prior applications are hereby incorporated herein in their entirety by reference.

TECHNICAL FIELD

The present invention relates to a method for selectively extracting membrane proteins using at least one calixarene.

The use of calixarenes in the method according to the invention enables the selective solubilization of the membrane proteins while preserving their three-dimensional structure which is essential to their enzymatic activity.

In the description below, the references in square brackets [ ] refer to the list of references presented at the end of the text.

STATE OF THE ART

The extraction of the membrane proteins is a prerequisite stage for their study in solution, in particular their structural characterization by radiocrystallography, which involves maintaining them in solution in a topological state identical to that which they adopt in the membranes.

In general, this stage is effected by means of detergents or surface-active which on the one hand make it possible to extract these proteins from their membrane environment, destructuring the membrane bilayer by entering into competition with the aliphatic chains of the lipids of which it is constituted and on the other hand maintain the membrane protein in solution on account of their hydrophilic component. However, these detergents do not display the same physico-chemical characteristics as the lipids and thus tend to destabilize the structure of the membrane domains, which is a source of structural heterogeneity.

Although they are the most effective for solubilizing the membrane proteins, the anionic detergents or surface-active agents, such as for example sodium dodecyl sulfate (SDS) or sodium desoxycholate, are generally destructuring. Moreover, the effectiveness of the phase of destructuring of the lipid bilayer is a function of the length of the aliphatic chain of the detergent or surfactant, a parameter which varies depending on the origin of the membranes and the proteins which are inserted into it.

Moreover, various studies concerning the interactions of various calixarenes with proteins are known but they do not make it possible to extract membrane proteins from their membrane environment, and in particular without denaturation of these.

In the context of the present invention, the terms "surface-active agent", "surfactant" and "detergent" are used indiscriminately to designate molecules having particular properties due to their amphiphilic structure. A molecule is described as amphiphilic when it simultaneously possesses a polar and hydrophilic group and an apolar and hydrophobic group.

The term "selective extraction" in the present invention signifies a method making it possible to extract the membrane proteins, selectively relative to one another from a membrane environment by solubilization of the lipid membranes in which these proteins are inserted, whether they are natural or artificial, and the bringing of said proteins into solution.

In the sense of the present invention, "solubilization" or "bringing into solution" of the membrane proteins is understood to mean the passage of the membrane protein from the membrane environment, in other words from an essentially lipid medium, to the aqueous environment. In the aqueous environment, the "solubilized" proteins can be in suspension, in dispersion or in the form of molecules which are not free in the aqueous solution. Said proteins can possibly be combined with or linked to surfactants or detergents.

At present, there are very few polyanionic detergents not denaturing to the membrane proteins, enabling their selective extraction.

There is thus a real need for an extraction method mitigating the defects, limitations, disadvantages and obstacles of the prior art, in particular for a method making use of anionic molecules having detergent properties making it possible to extract the membrane proteins selectively without denaturing them, in other words without destructuring them or modifying their normal three-dimensional conformation which makes it possible for them to fulfill their function.

DESCRIPTION OF THE INVENTION

The purpose of the present invention is precisely to respond to this need by providing a method for selectively extracting membrane proteins comprising a stage which consists of contacting an aqueous solution of the membrane protein to be extracted with at least one calixarene of formula (I):

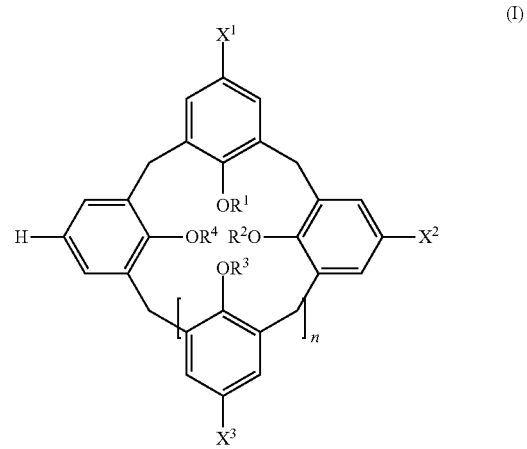

wherein:
  n is a integer equal to 1, 3, 5 or 6;
  $R^1$, $R^2$, $R^3$ and $R^4$ independently of one another represent a hydrogen atom, a linear or branched ($C_{1-12}$) alkyl group (for example ($C_{3-12}$) alkyl, for example ($C_{9-12}$) alkyl) possibly substituted with one or more hetero atoms selected from the group of O, S, N and P atoms, a linear or branched ($C_{1-12}$) alkyl group (for example ($C_{3-12}$) alkyl, for example ($C_{9-12}$) alkyl), possibly substituted with a —COOR group where R is a linear or branched ($C_{1-4}$ alkyl group, or an aryl group comprising from 6 to 20 carbon atoms; and
  $X^1$, $X^2$, and $X^3$ independently of one another represent a —$(CH_2)_m$—COOR' group in which
    m is a integer ranging from 0 to 10, and R' represents a hydrogen atom or a linear or branched ($C_{1-4}$) alkyl group;

or one of the pharmaceutically acceptable salts thereof.

According to one particular implementation mode of the invention, the method for selective extraction of the membrane protein can be carried out using at least one calixarene of formula (I) in which:

n is a integer equal to 1;

$R^1$, $R^2$, $R^3$ and $R^4$ independently of one another represent a hydrogen atom or a linear or branched ($C_{1-12}$) alkyl group; and $X^1$, $X^2$ and $X^3$ independently of one another represent a —$(CH_2)_m$—COOR' group in which m is a integer ranging from 0 to 10, and R' represents a hydrogen atom;

or one of the pharmaceutically acceptable salts.

In the sense of the present invention "alkyl" is understood to mean a linear, branched or cyclic, saturated or unsaturated, possibly substituted carbon-containing radical comprising 1 to 12 carbon atoms. As an indication, the methyl, ethyl, propyl, butyl, isobutyl, pentyl, hexyl, octyl, nonyl, decyl, undecyl and dodecanyl radicals and branched isomers thereof can be cited. The alkyl group can possibly be substituted with one or more hetero atoms selected from the group of O, S, N, P atoms.

The term "aryl" designates in a general manner a cyclic aromatic substituent containing from 6 to 20 carbon atoms. In the context of the invention the aryl group can be mono- or polycyclic and possibly substituted. As such, benzyl and phenyl can be cited.

In the context of the present invention, the term "pharmaceutically acceptable salts" comprises the salts prepared with non-toxic acids or bases, depending on the substituents present on the compounds. When the compounds of the invention contain acidic functions, the corresponding salts can be obtained by addition of an organic or inorganic base to the compound in neutralized form possibly in the presence of a preferably inert solvent. Examples of addition salts of a base can be the sodium, potassium, calcium, ammonium, amino (organic), or magnesium salts. When the compounds of the invention contain basic functions, the corresponding salts can be obtained by addition of an organic or inorganic acid possibly in a preferably inert solvent. Examples of inorganic acid addition salts can be the hydrochloride, hydrobromide, nitrate, carbonate, monohydrogen carbonate, phosphate, monohydrogen phosphate, dihydrogen phosphate, sulfate, monohydrogen sulfate or hydriodide salts. Examples of organic acid addition salts can be the acetate, propionate, isobutyrate, maleate, malonate, benzoate, succinate, suberate, fumarate, lactate, mandelate, phthalate, benzenesulfonate, p-tolylsulfonate, citrate, tartrate or methanesulfonate salts.

In the sense of the present invention "membrane protein" is understood to mean a protein associated with biological membranes, in other words either anchored, or integral, and not free for diffusion in aqueous media and unstable in those media. Among the membrane proteins, for example the proteins of plasma membranes and the proteins of intracellular membranes (such as for example the proteins of mitochondrial, nuclear and lysosomal membranes, etc.) can be cited.

The membrane proteins are often classified on the basis of the structures which enable them to interact with the membranes and the manner in which these structures fit together. The membrane proteins can be polytopic proteins or monotopic proteins, for example polytopic proteins.

"Polytopic proteins" is understood to mean proteins which pass through the membrane one or more times.

"Monotopic proteins" is understood to mean proteins which interact with only one side of the membrane.

The membrane proteins can also be classified on the basis of the difficulty of extracting from the membranes. They can be integral or peripheral, for example integral.

"Integral proteins" is understood to mean monotopic or polytopic proteins which interact strongly with the membrane, in particular by hydrophobic interactions. These proteins are also called "intrinsic proteins".

"Peripheral proteins" is understood to mean monotopic proteins which interact weakly with the membrane, in other words either by electrostatic bonds, or by the involvement of other membrane proteins. These proteins are also called "extrinsic proteins".

In the sense of the present invention, "aqueous solution of the membrane protein" is understood to mean an aqueous solution comprising one or more membrane protein(s). This can for example be a suspension or a dispersion, wherein the proteins can be in a non-dissolved or non-diffuse form or can for example be combined with a biological membrane fraction.

The calixarenes of formula (I) are anionic molecules having detergent properties. They possess a hydrophilic face made up of several carboxylate functions and a hydrophobic face made up of alkyl groups. The multiplicity of negative charges on the one hand encourages the ionic interaction of the detergent molecule with the hydrophilic surface of the protein and on the other hand prevents its (destructuring) penetration to the (hydrophobic) core of the proteins.

More precisely, on account of their chemical formula the calixarenes of formula (I) have a molecular geometry in the shape of a cone or truncated cone, in which the flared region is hydrophilic whereas the tail is hydrophobic (FIG. 1). This particular shape of the calixarenes of formula (I) enables the formation of micelles, which on the one hand encourage the passage of the proteins from a membrane environment towards an aqueous medium, and on the other hand enable the conservation of their three-dimensional structure and hence of their activity.

Thus the use of the calixarenes of formula (I) in the method according to the invention makes it possible to extract the membrane proteins selectively by solubilizing them selectively (in other words by enabling their passage from the membrane environment to the aqueous environment) while preserving their three-dimensional structure which is essential to their activity, for example enzymatic. Thus, after their reconstitution in natural or synthetic lipids, the membrane proteins recover their activity.

Moreover, the method of the invention enables the extraction of a given protein, selectively relative to other membrane proteins, in particular by modulating the length of the hydrophobic tail of the calixarene. The method of the invention thus enables the extraction and the separation of fractions of membrane proteins (solubilized fractions and non-solubilized fractions). In fact, depending on the substituents present, in particular the length of the alkyl groups in $R^1$, $R^2$, $R^3$ and/or $R^4$, the calixarenes of formula (I) can be adjusted to the types of membranes and proteins and can make it possible to perform a selective and effective extraction and solubilization.

According to one particular implementation mode of the invention, the method of the invention can comprise two or more successive stages of contacting with different calixarenes of formula (I), which enables the extraction and isolation of some membrane proteins relative to others.

In addition, on account of their structure, in particular the nature of the substituents $X^1$, $X^2$ and/or $X^3$, the calixarenes according to the invention can form micelles the existence whereof is modulable depending on the pH. This property is particularly useful for encouraging or conversely discouraging the formation of micelles and thus maintaining a membrane protein in solution with detergents at different degrees of organization. In fact, the absence of micelles encourages the establishment of protein-protein contacts which facilitate the formation of crystals in solution.

The method of the invention makes it possible to extract any membrane protein, and advantageously any membrane protein present in a biological membrane fraction derived from a prokaryotic or eukaryotic, healthy or impaired organism. For example, in the method according to the invention, the membrane protein to be extracted can be in a plasma membrane fraction derived from a prokaryotic or eukaryotic, healthy or impaired organism. For example, the method of the invention makes it possible to extract any polytopic membrane protein. For example, the method of the invention makes it possible to extract any integral membrane protein.

According to one implementation mode of the invention, the membrane protein can be selected from the group comprising the transport proteins. In the sense of the present invention, "transport protein", is understood to mean a membrane protein whose role is the transport of various substances (ions, sterols, macromolecules, etc.) on both sides of the membrane. For example the ABC transporters (ATP-binding Cassette in English or protein with ATP-binding domain in French), receptors, exchangers, channels, etc. can be cited.

According to one particular implementation mode of the invention, the transport protein can be an ABC transporter selected from the group comprising P glycoprotein (Pgp/ABCB1) [1], MRP1/ABCC1 (multidrug resistance protein, human polytopic and integral ABC transporter) [2], BCRP/ABCG2 (breast cancer resistance protein, human polytopic and integral ABC transporter) [3], BmrA (Bacterial multidrug resistance ATP, prokaryotic polytopic and integral ABC transporter) [4].

Preferably, the membrane protein is a protein selected from the group comprising, as transport proteins, glycoprotein P (Pgp/ABCB1), MRP1/ABCC1, BCRP/ABCG2, and all proteins of that class. More particularly, the transport protein can be an ABC transporter selected from the group comprising BmrA.

The stage of contacting an aqueous solution comprising the membrane protein to be extracted with at least one calixarene of formula (I) can be effected at a pH ranging from 5.5 to 10, preferably from 6 to 9.

The extraction method can be effected at a temperature ranging from 0 to 100° C., preferably from 4 to 25° C.

The extraction method utilizes a concentration of calixarene of formula (I) ranging from $10^{-6}$ to $10^{-2}$ M.

The method of the extraction according to the invention can be effected with calixarenes in solution or calixarenes in colloidal aggregates on account of their surface-active property.

In the sense of the present invention, colloidal aggregate is understood to mean groups of a few to a few hundred molecules of calixarene organizing themselves on the basis of forces of repulsion towards the solvent. Given their nature, the calixarenes of formula (I) are capable of forming aggregates in an appropriate medium such as for example in water, in an aqueous solution, in an isotonic medium or in a biological medium.

The aggregate can be selected from the group comprising micelles, liposomes and lipid nanoparticles. Preferably, the calixarenes are in the form of micelles.

The term micelle designates a spheroidal aggregate of molecules of calixarene of formula (I) which organizes itself depending on the solvent used. For example in water or an aqueous solvent, the lipophilic ends are turned towards the interior of the micelle whereas the hydrophilic ends form the interface of the micelle with the solvent. In an organic solvent, for example oil, the arrangement is reversed.

The term liposome designates small artificially made vesicles in particular constituted of thin sheets of phospholipids, separated from one another by aqueous compartments. They can have a structure very close to that of cell membranes.

In the context of the present invention, the term nanoparticle signifies an assembly of a few hundred to a few thousand molecules of calixarene of formula (I), resulting in an object at least one of whose dimensions is of nanometer size, for example between 1 and 300 nm.

In the method of the invention, the stage of contacting an aqueous suspension comprising the membrane protein to be extracted with the calixarene of formula (I) can possibly be effected in the presence of at least one co-solute selected from the group comprising,
i) organic and inorganic salts selected from the group comprising the pharmaceutically acceptable salts;
ii) small biologically active molecules selected from the group of the amino acids, vitamins, lipids, steroids, carbohydrates or metabolites;
iii) oligomeric biologically active molecules selected from the group of the peptides, oligonucleotides or oligosaccharides; and
iv) polymeric biological molecules selected from the group of the proteins, polynucleotides and polysaccharides.

According to one implementation mode of the invention, the contacting stage can be preceded by a stage in which:
    the membrane protein to be extracted or the membrane fraction containing it is solubilized in a buffer solution, and
    the calixarene of formula (I) is added in accordance with the temperature, pH and concentration conditions previously described.

According to one implementation mode of the invention, the contacting stage can be followed by a centrifugation stage, making it possible to separate the membrane proteins complexed with the calixarenes of formula (I) from the non-complexed membrane proteins.

The membrane proteins complexed with the calixarenes of formula (I) and the non-complexed membrane proteins can be separated by centrifugation, for example for 1 hr, at 4° C. and at a speed of 100 000×g. The centrifugation conditions will depend on the nature of the protein. Those skilled in the art will know how to select the optimal centrifugation conditions, for example described in [6].

Other advantages may also be seen by those skilled in the art on reading the examples below, illustrated by the appended diagrams, which are given for illustration.

BRIEF DESCRIPTION OF DIAGRAMS

FIG. 1 shows the cone-shaped geometry of the calixarenes used in the method of the invention. The polar group at the top is shown dark and the hydrophobic aliphatic chain is located at the bottom of the diagram. This special geometry makes the formation of micelles possible. In FIG. 1, the region A corresponds to the charged hydrophilic region, the region B corresponds to the platform of the calix[4]arene and the region C corresponds to an aliphatic $C_nH_{2n+1}$ tail.

FIG. 2 shows the surfactant (or surface-active) properties of p(COOH)$_3$—Ar4-o($C_nH_{2n+1}$) molecules, n=1-12. The effect of the derivatives of calix[4]arene containing alkyl chains with 1 to 12 carbon atoms on the surface tension of water was followed as a function of the concentration of said derivatives (molar M or mol/L) at pH 6.0 (not exposed) and 8.0 (exposed). The surface-active properties of DDM (β-D-dodecyl malto-pyranoside) are also shown in this figure. Each point corresponds to the mean of three values.

FIG. 3 shows the surfactant potential of the $p(COOH)_3$—$Ar4$-$o(C_nH_{2n+1})$ molecules as a function of the length of the alkyl chains (n=number of carbon atoms=1-12) and the pH. The effect of the molecules containing an alkyl chain having from 1 to 12 methylene groups (n, x axis in FIG. 3) on the surface tension of water was measured at a concentration of $10^{-2}$M, at pH 6.0 (open circles) and at pH 8.0 (squares). Each point corresponds to the mean of three values.

FIG. 4 shows the Critical Micellar Concentration (CMC) of the series $p(COOH)_3$—$Ar4$-$o(C_nH_{2n+1})$, n=1-12 as a function of the pH and the length of the alkyl chains. The effect of the molecules having an alkyl chain with 1 to 12 methylene groups (m, x axis in the figure) on the CMC is measured at a concentration of $10^{-2}$ M, at pH 6.0 (solid circles) and 8.0 (open circles). Each point corresponds to the mean of three values, estimated from the data from FIG. 2.

FIG. 5 shows the modulation of the surfactant potential of the compound $p(COOH)_3$—$Ar4$-$o(C_7H_{15})$ by amino acids (aa). The compound $p(COOH)_3$—$Ar4$-$o(C_7H_{15})$ is present at a concentration of $10^{-2}$ M whereas that of the amino acids vary as indicated. The surface tension is measured at pH 8.0. The amino acids are indicated by their three-letter code: Glu=glutamic acid, Trp=tryptophan, Asn=asparagine, Gly=glycine, Ala=alanine, Ser=serine, Phe=phenylalanine, Leu=leucine, Pro=Proline, Lys=lysine, His=histidine, Arg=arginine. Each point corresponds to the mean of three values.

FIG. 6 shows the topological diagram of BmrA expressed in a bacterium and inserted into its plasma membrane. BmrA is a homodimeric protein, each monomer being made up of a transmembrane domain (TMD) linked to a nucleotide-binding domain (NBD) [4, 5].

FIG. 7 shows the tests of solubilization of membranes enriched in BmrA with the $p(COOH)_3$—$Ar4$-$o(C_nH_{2n+1})$ molecules and other known detergents. The membrane fractions are prepared as indicated in example 11 and analyzed after incubation either with $p(COOH)_3$—$Ar4$-$o(C_nH_{2n+1})$ molecules, n=1 to 12 as indicated in FIG. 7 or with known detergents (FC12, FosCholine 12: n-dodecylphosphocholine, zwitterionic detergent; SDS: sodium dodecylsulfate, strong anionic detergent; DDM: n-dodecyl-β-D-maltopyranoside, uncharged detergent), or with a buffer (No Det). After separation of the solubilized (S, supernatant) and non-solubilized (P, pellet or plug) protein by centrifugation at 100 000×g, 1 hr, 4° C., the protein content is analyzed by SDS PAGE. The gray and black dotted lines and the black line serve as a scale of the efficacy of the molecules to be solubilized. The "no det" lines signify "without detergent".

FIG. 8 shows the effect of the concentration of the $p(COOH)_3$—$Ar4$-$o(C_nH_{2n+1})$ molecules on the solubilization of BmrA. The experimental conditions are those of FIG. 7, with the exception of the concentrations of the butyl, heptyl and dodecyl molecules which are as indicated in the figure, for which the g/L<->M correspondence is indicated in Table 2. The "no det" lines signify "without detergent".

FIG. 9 shows the effect of solubilization by $p(COOH)_3$—$Ar4$-$o(C_nH_{2n+1})$ series on the ATPase activity of BmrA. The solubilization tests take place as in FIG. 8 and the ATPase activity tests are described in example 11. The vertical dotted lines show the CMC of each compound. The black lozenges correspond to a test in which BmrA is solubilized with $p(COOH)_3$—$Ar4$-$o(C_7H_{15})$ then reconstituted in lipids after removal of the detergent with biobeads (Bio-Rad) according to the procedure described in Lenoir et al. [6]. The y axis shows the specific activity in %, 100% activity corresponding to 0.25 μmol Pi produced/mg protein/min.

BmrA Mb: activity of BmrA in natural membranes,
DDM sup./DDM: activity of BmrA in the DDM extract,
DDM sup./Lip.: activity of BmrA from the DDM extract and reconstituted in liposomes,
FC12 sup./FC12: activity of BmrA in the Foscholine 12 extract,
FC12 sup./Lip.: activity of BmrA from the Foscholine 12 extract and reconstituted in liposomes,
C4C7 sup./FC12: activity of BmrA in the calixarene C4C7 (in other words calix[4]arene-O-heptyloxy) extract,
C4C7 sup./Lip.: activity of BmrA from the calixarene C4C7 extract and reconstituted in liposomes.

Figure 12:
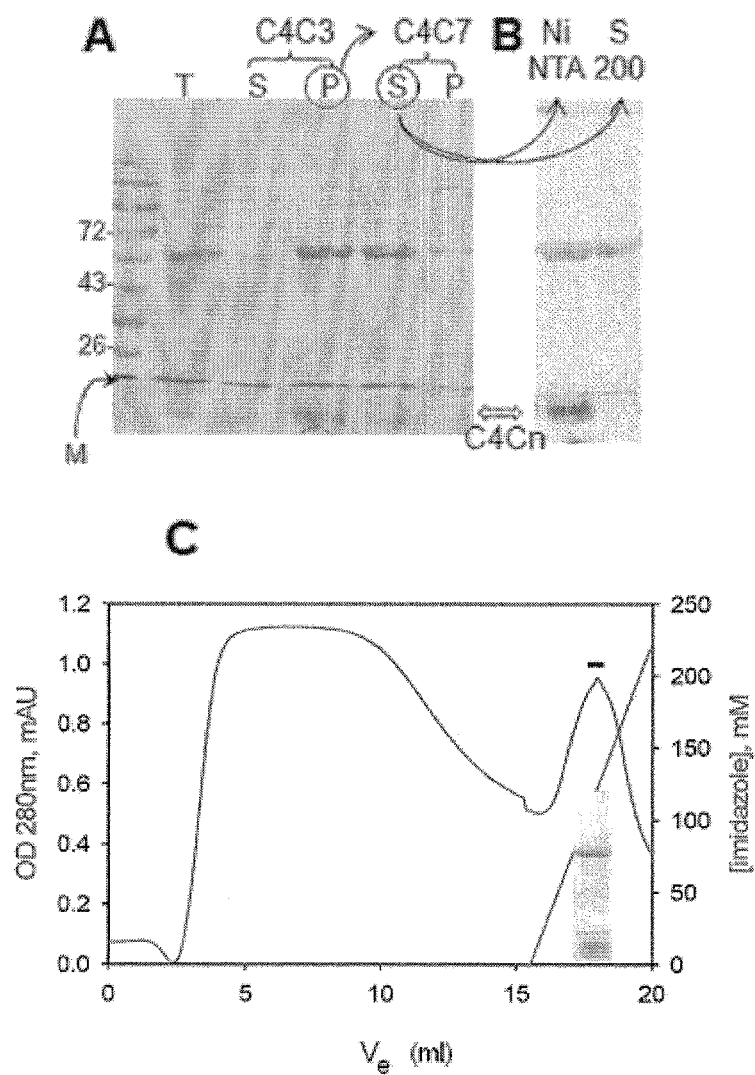
Figure 12:
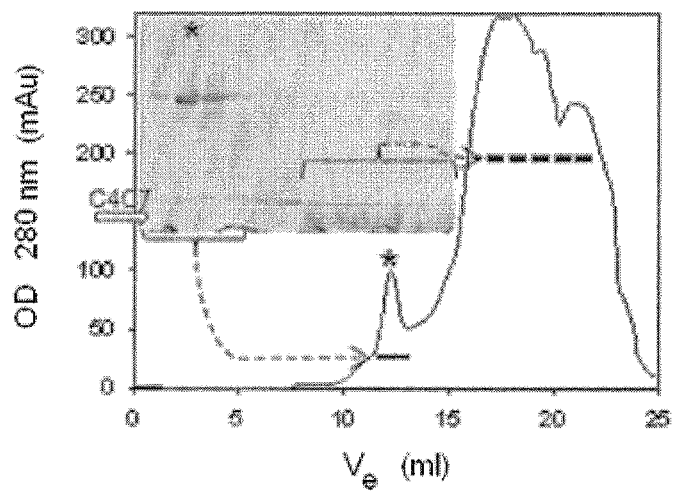
Figure 12:
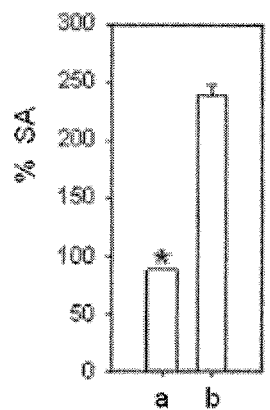

FIG. 12 summarizes the results of an extraction successively using the calixarenes C4C3 then C4C7 (FIG. 12A) followed by purification by gel filtration chromatography (FIGS. 12B-E). FIG. 12A shows the SDS-PAGE (SDS-polyacrylamide gel electrophoresis) of the solubilized (S, supernatant) and non-solubilized (P, plug) fractions after successive extractions by the calixarenes C4C3 then C4C7, M representing the migration front. FIG. 12C shows the nickel-affinity chromatography after extraction by the calixarene C4C7, as a function of the elution volume $V_e$ in milliliters. FIG. 12D shows the gel filtration chromatography in the presence of FC12 after extraction by the calixarene C4C7, as a function of the elution volume $V_e$ in milliliters. FIG. 12E shows the specific ATPase activity (sensitive to vanadate) for fraction a ("S200 pool FC12" or fraction of BmrA subjected to gel filtration chromatography in the presence of foscholine 12) and fraction b ("S200 pool Lip.", the same fraction of BmrA subjected to gel filtration then reconstituted in the presence of liposomes).

Figure 13:
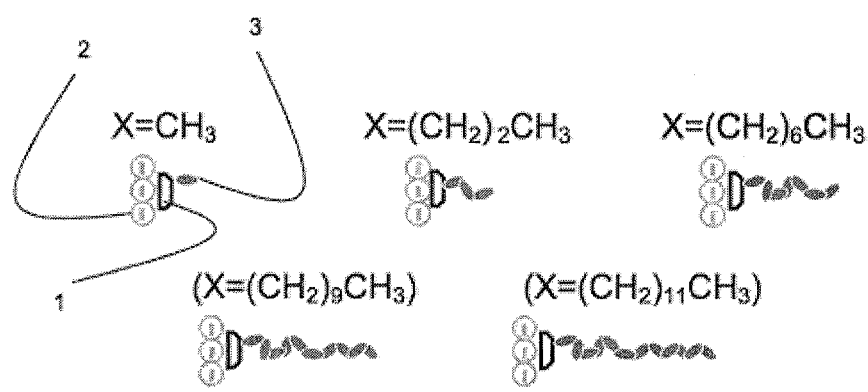
Figure 13:
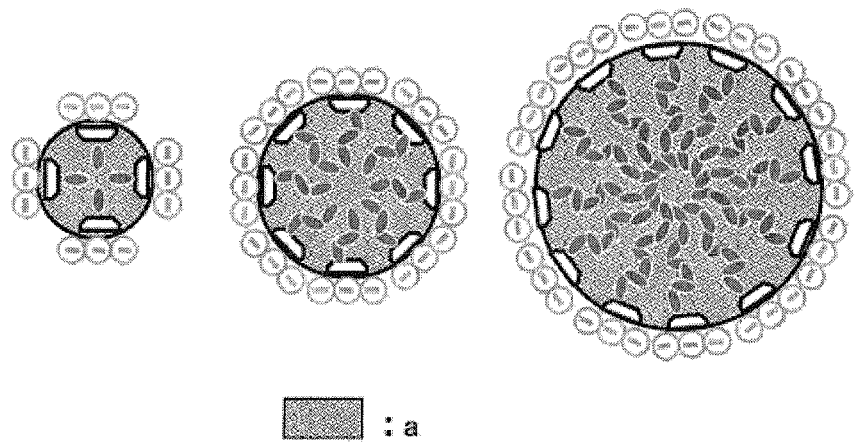

FIG. 13 shows different calix[4]arenes (FIG. 13A) and examples of supramolecular organization of these molecules into micelles or supramolecular clusters (FIG. 13B).

EXAMPLES

General Methods
Solvents and Reagents

The dichloromethane ($CH_2Cl_2$) and the toluene are distilled under a nitrogen atmosphere over $CaH_2$, and the tetrahydrofuran (THF) is distilled under a nitrogen atmosphere over sodium and benzophenone. The diethyl ether is distilled under a nitrogen atmosphere over $CaH_2$ and stored over 4 Å molecular sieve at 0-4° C. under nitrogen. The other solvents used are obtained from the supplier Carlo-Erba.

Nuclear Magnetic Resonance (NMR)

The $^1H$ and $^{13}C$ spectra are run on a Bruker AV500 instrument. The chemical shifts (δ) of the $^1H$ NMR spectra are calibrated according to the reference tetramethylsilane (TMS) having a δ value of 0.00 ppm. The δ of the $^{13}$C NMR spectra are calibrated on the reference value of the solvent.

The measurements are performed at 25° C. in tubes of 5 mm diameter. The spectra are run in deuterated solvents obtained from the supplier Aldrich or SDS.

Chromatography

The thin layer chromatograms (TLC) are run on Merck "TLC Silica gel 60F$_{254}$" aluminum plates. The compounds are revealed under a UV (Ultra-Violet) lamp or/and are dipped in the developer containing phospho-molybdic acid in sulfuric acid and ethanol followed by heating with a heat stripper.

The chromatography columns are made up with a Merck silica gel (Silica gel 60 (40-63 μm)).

Mass Spectrometry

ESI mass: the samples are analyzed on a Perkin Elmer Sciex API 300 spectrometer in solvents of "analytical reagent" quality.

Surface Tension Measurement

The surfactant properties of the calixarenes of formula (I) are evaluated in a 1 ml sitting drop by means of a Kibron micro-depression instrument and using a stainless steel syringe and a Wilhelmy balance. The curves obtained are processed with the software Sigmaplot v11.

Example 1

Synthesis of 25-butyloxycalix[4]arene

To a suspension of calix[4]arene (20 g, 0.47 mol) in anhydrous DMF (943 ml) were added solutions of CsF (8.49 g, 1.2 equivalents) and iodobutane (35.47 ml, 10 equivalents). The reaction mixture is stirred at 40° C. for 96 hrs. The progress of the reaction is followed by TLC (Thin Layer Chromatography). Once the reaction has ended, it is stopped by addition of 1M hydrochloric acid (250 ml). The reaction medium is extracted with CH$_2$Cl$_2$ (2×200 ml). The organic phases are combined, washed with water (2×250 ml) and dried over MgSO$_4$. After evaporation of the solvent, the crude product remaining is taken up in a CH$_2$Cl$_2$/MeOH mixture (1:1). The solution is then filtered to remove the calix[4]arene which has not reacted and purified by column chromatography (CH$_2$Cl$_2$/hexane 1:1).

A white solid is obtained in a yield of 68% by the procedure M.Pt.=239° C.;

$^1$H NMR (CDCl$_3$) δ 1.14 (t, 3H, $^2J_{H-H}$=7.1 Hz, Ar—OCH$_2$CH$_2$CH$_2$CH$_3$), 1.74 (m, 2H, Ar—O(CH$_2$)$_2$ CH$_2$CH$_3$), 2.18 (m, 2H, Ar—OCH$_2$CH$_2$CH$_2$CH$_3$), 3.48 (d, 4H, $^2J_{H-H}$=13.3 Hz, Ar—CH$_2$—Ar), 4.17 (t, 2H, $^2J_{H-H}$=7.0 Hz, Ar—OCH$_2$ (CH$_2$)$_2$CH$_3$), 4.30 (d, 2H, $^2J_{H-H}$=13.6 Hz, Ar—CH$_2$—Ar), 4.37 (d, 2H, $^2J_{H-H}$=12.9 Hz, Ar—CH$_2$—Ar), 6.69-7.07 (m, 12H, Ar—H), 9.46 (s, 2H, Ar—OH), 9.77 (s, 1H, Ar—OH).

$^{13}$C NMR (CDCl$_3$) δ 14.2 (Ar—O(CH$_2$)$_3$CH$_3$), 19.2 (Ar—O(CH$_2$)$_2$CH$_2$CH$_3$), 19.7 (Ar—OCH$_2$CH$_2$CH$_2$CH$_3$), 31.4 and 32.3 (Ar—CH$_2$—Ar); 77.1 (Ar—OCH$_2$(CH$_2$)$_2$CH$_3$), 120.8; 121.8; 121.7; 126.1; 128.3; 128.7; 129.3 (Ar), 149.1 and 150.6 (ArC—OH), 151.5 (ArC—O(CH$_2$)$_3$CH$_3$).

ES mass spectrum (CHCl$_3$) m/z: 481.2 [M+H]$^+$, 503.3 [M+Na]$^+$, 519.2 [M+K]$^+$.

Example 2

Synthesis of 25-dodecyloxycalix[4]arene

To a suspension of calix[4]arene (20 g, 0.47 mol) in anhydrous DMF (943 ml) were added solutions of CsF (8.49 g, 1.2 equivalents) and iodododecane (35.47 ml, 10 equivalents). The reaction mixture is stirred at 40° C. for 96 hrs. The progress of the reaction is followed by TLC. Once the reaction has ended, it is stopped by addition of 1M hydrochloric acid (250 ml). The reaction medium is extracted with CH$_2$Cl$_2$ (2×200 ml). The organic phases are combined, washed with water (2×250 ml) and dried over MgSO$_4$. After evaporation of the solvent, the crude product remaining is taken up in a CH$_2$Cl$_2$/MeOH mixture (1:1). The solution is then filtered to remove the calix[4]arene which has not reacted and purified by column chromatography (CH$_2$Cl$_2$/hexane 1:1).

A white solid is obtained in a yield of 48%, M.Pt.=235° C.;

$^1$H NMR (CDCl$_3$) δ 1.01 (t, 3H, $^3J_{H-H}$=7.0 Hz, Ar—O (CH$_2$)$_{11}$CH$_3$), 1.42 (m, 4H, Ar—O(CH$_2$)$_8$CH$_2$CH$_2$CH$_3$), 1.49 (m, 4H, A—O—(CH$_2$)$_7$CH$_2$CH$_2$(CH$_2$)$_2$CH$_3$), 1.53 (m, 4H, Ar—O(CH$_2$)$_5$CH$_2$CH$_2$(CH$_2$)$_4$CH$_3$), 1.62 (m, 4H, Ar—O (CH$_2$)$_3$CH$_2$CH$_2$(CH$_2$)$_6$CH$_3$), 1.80 (m, 2H, Ar—O(CH$_2$)$_2$ CH$_2$(CH$_2$)$_8$CH$_3$), 2.29 (m, 2H, Ar—OCH$_2$CH$_2$(CH$_2$)$_9$CH$_3$), 3.57 (d, 4H, $^2J_{H-H}$=13.3 Hz, Ar—CH$_2$—Ar), 4.26 (t, 2H, $^2J_{H-H}$=6.8 Hz, Ar—OCH$_2$(CH$_2$)$_{10}$CH$_3$), 4.39 (d, 2H, $^2J_{H-H}$=13.1 Hz, Ar—CH$_2$—Ar), 4.48 (d, 2H, $^2J_{H-H}$=13.1 Hz, Ar—CH$_2$—Ar), 6.77-7.18 (m, 12H, Ar—H), 9.57 (s, 2H, Ar—OH), 9.88 (s, 1H, Ar—OH).

$^{13}$C NMR (CDCl$_3$) δ 14.3 (Ar—O(CH$_2$)$_{11}$CH$_3$), 22.9 (Ar—O(CH$_2$)$_{10}$CH$_2$CH$_3$), 26.1 (Ar—O(CH$_2$)$_9$ CH$_2$CH$_2$CH$_3$), 29.6 (Ar—O(CH$_2$)$_8$CH$_2$(CH$_2$)$_2$CH$_3$), 29.7 (Ar—O(CH$_2$)$_7$CH$_2$(CH$_2$)$_3$CH$_3$), 29.8 (Ar—O(CH$_2$)$_6$CH$_2$ (CH$_2$)$_4$CH$_3$), 29.8 (Ar—O(CH$_2$)$_5$CH$_2$(CH$_2$)$_5$CH$_3$), 29.9 (Ar—O(CH$_2$)$_4$CH$_2$(CH$_2$)$_6$CH$_3$), 30.1 (Ar—O(CH$_2$)$_3$CH$_2$ (CH$_2$)$_7$CH$_3$), 31.6 (Ar—O(CH$_2$)$_2$CH$_2$(CH$_2$)$_8$CH$_3$), 31.8 (Ar—OCH$_2$CH$_2$(CH$_2$)$_9$CH$_3$), 32.1 and 32.2 (Ar—CH$_2$—Ar), 77.7 (Ar—OCH$_2$(CH$_2$)$_{10}$CH$_3$) 121.1; 122.1; 122.4; 126.2; 128.4; 128.6; 128.9; 129.1; 129.5; 134.4 (Ar), 149.4 and 151.0 (ArC—OH), 151.6 (ArC—O(CH$_2$)$_{11}$CH$_3$).

ES mass spectrum (CHCl$_3$) m/z: 593.2 [M+H]$^+$, 615.2 [M+Na]$^+$, 631.3 [M+K]$^+$.

Example 3

Synthesis of 5,11,17 tris-[(carboxylato)methyl]25-mono-methyloxy 26,27,28 tris-hydroxycalix[4]arene—compound 5a 5 g of tris-[(cyano)methyl]monomethyloxy26,27,28 tris-hydroxycalix-[4]arene in 50 ml of EtOH are placed in a flask. 50 ml of 3M KOH are added. The reaction mixture is heated under reflux for 72 hrs. The solution is cooled, treated with 500 ml of iced water, and acidified with a 12N HCl solution. The yellow product is recovered by filtration and placed then brought to reflux for 72 hrs in 50 ml of MeOH and 4.5 g of NaOH in 50 ml of water. The solution is then cooled, treated with 250 ml of iced water, acidified with HCl, filtered and washed with water to yield the 5,11,17 tris-[(carboxy)methyl] 25-monomethyloxycalix[4]arene in the form of an off-white to yellow powder in a yield of 72%.

M.Pt.=221° C., $^1$H NMR (DMSO) δ 3.24 (s, 2H, Ar—CH$_2$COOH), 3.31 (s, 4H, Ar—CH$_2$COOH), 3.39 (d, 2H, $^2J_{H-H}$=Hz, Ar—CH$_2$—Ar), 3.48 (d, 2H, $^2J_{H-H}$=13.2 Hz, Ar—CH$_2$—Ar), 4.01 (s, 3H, Ar—OCH$_3$), 4.18 (d, 2H, $^2J_{H-H}$=13.2 Hz, Ar—CH$_2$—Ar), 4.25 (d, 2H, $^2J_{H-H}$=13.2 Hz, Ar—CH$_2$—Ar), 6.89-7.16 (m, 9H, Ar—H), 8.79 (s, 2H, Ar—OH), 9.50 (s, 1H, Ar—OH), 12.07 (s, 3H, Ar—CH$_2$—COOH), $^{13}$C NMR (DMSO) δ 21.1 (Ar—CH$_2$—COOH), 29.1 and 30.9 (Ar—CH$_2$—Ar), 66.1 (Ar—OCH$_3$), 142.7; 143.1; 147.4; 148.4 (Ar), 150.3 and 153.5 (ArC—OH), 154.1 (ArC—OCH$_3$), 168.4 and 169.3 (Ar—CH$_2$—COOH).

ES mass spectrum (DMSO) m/z: 613.1 [M+H]+, 635.1 [M+Na]+, 611.3 [M–H]−.

Example 4

Synthesis of 5,11,17 tris-[(carboxylato)methyl]25-mono-butyloxy 26,27,28 tris-hydroxycalix[4]arene—compound 5b 5 g of tris-[(cyano)methyl]monobutyloxy26,27,28 tris-hydroxycalix-[4]arene in 50 ml of EtOH are placed in a flask. 50 ml of 3M KOH are added. The reaction mixture is heated under reflux for 72 hrs. The solution is cooled, treated with 500 ml of iced water, and acidified with a 12N solution of HCl. The yellow product is recovered by filtration then brought to reflux for 72 hrs in 50 ml of MeOH and 4.5 g of NaOH in 50 ml of water. The solution is cooled, treated with 250 ml of iced water) acidified with HCl, filtered and washed with water to yield the 5,11,17 tris-[(carboxy)methyl]25-monobutyloxycalix[4]arene in the form of an off-white to yellow powder in a yield of 75%.

M.Pt.=223° C., $^1$H NMR (DMSO) δ 1.07 (t, 3H, $^2J_{H-H}$=6.9 Hz, Ar—O(CH$_2$)$_3$CH$_3$), 1.69 (m, 2H, Ar—O(CH$_2$)$_2$CH$_2$CH$_3$), 2.01 (m, 2H, Ar—OCH$_2$CH$_2$CH$_2$CH$_3$), 3.17 (s, 2H, Ar—CH$_2$COOH), 3.31 (s, 4H, Ar—CH$_2$COOH), 3.38 (d, 2H, $^2J_{H-H}$=13.1 Hz, Ar—CH$_2$—Ar), 3.48 (d, 2H, 2H, $^2J_{H-H}$=13.1 Hz, Ar—CH$_2$—Ar), 3.57 (t, 2H, $^2J_{H-H}$=Hz, Ar—OCH$_2$(CH$_2$)$_2$CH$_3$), 4.11 (d, 2H, $^2J_{H-H}$=13.1 Hz, Ar—CH$_2$—Ar), 4.20 (d, 2H, $^2J_{H-H}$=13.1 Hz, Ar—CH$_2$—Ar), 6.82-7.12 (m, 9H, Ar—H), 8.87 (s, 2H, Ar—OH), 9.56 (s, 1H, Ar—OH), $^{13}$C NMR (DMSO) δ 13.8 (Ar—O(CH$_2$)$_3$CH$_3$), 18.6 (Ar—O(CH$_2$)$_2$CH$_2$CH$_3$), 22.1 (Ar—CH$_2$—COOH), 30.3 (Ar—OCH$_2$CH$_2$CH$_2$CH$_3$), 30.6 and 31.4 (Ar—CH$_2$—Ar), 76.6 (Ar—OCH$_2$(CH$_2$)$_2$CH$_3$), 125.7; 127.6; 128.7, 130.1; 134.0 (Ar), 147.8 and 150.0 (ArC—OH), 151.9 (ArC—O(CH$_2$)$_3$CH$_3$), 172.9 (Ar—CH$_2$—COOH).

ES mass spectrum (DMSO) m/z: 677.1 [M+Na]+, 653.3 [M–H]−.

Example 5

Synthesis of 5,11,17 tris-[carboxylato)methyl]25-mono-hexyloxy 26,27,28 tris-hydroxycalix[4]arene—compound 5c 5 g of tris-[(cyano)methyl]monohexyloxy26,27,28 tris-hydroxycalix-[4]arene in 50 ml of EtOH are placed in a flask. 50 ml of 3M KOH are added. The reaction mixture is heated under reflux for 72 hrs. The solution is cooled, treated with 500 ml of iced water, and acidified with a 12M solution of HCl.

The yellow product is recovered by filtration then brought to reflux for 72 hrs in 50 ml of MeOH and 4.5 g of NaOH in 50 ml of water. The solution is cooled, treated with 250 ml of iced water, acidified with HCl, filtered and washed with water to yield the 5,11,17 Tris-[(carboxy)methyl]25-mono-hexyloxycalix[4]arene in the form of a yellow solid in a yield of 69%.

M.Pt.=222° C., $^1$H NMR (DMSO) δ 0.95 (t, 3H, $^2J_{H-H}$=7.1 Hz, Ar—O(CH$_2$)$_5$CH$_3$), 1.42 (m, 4H, Ar—O(CH$_2$)$_3$CH$_2$CH$_2$CH$_3$), 1.67 (m, 2H, Ar—O(CH$_2$)$_2$CH$_2$(CH$_2$)$_2$CH$_3$), 2.02 (m, 2H, Ar—CH$_2$CH$_2$(CH$_2$)$_3$CH$_3$), 3.16 (s, 2H, Ar—CH$_2$—COOH), 3.31 (s, 4H, Ar—CH$_2$—COOH), 3.38 (d, 2H, $^2J_{H-H}$=12.9 Hz, Ar—CH$_2$—Ar), 3.50 (d, 2H, $^2J_{H-H}$=12.9 Hz, Ar—CH$_2$—Ar), 4.04 (t, 2H, $^2J_{H-H}$=7.2 Hz, Ar—OCH$_2$(CH$_2$)$_4$CH$_3$), 4.15 (d, 2H, $^2J_{H-H}$=12.9 Hz, Ar—CH$_2$—Ar), 4.20 (d, 2H, $^2J_{H-H}$=12.9 Hz, Ar—CH$_2$—Ar), 6.85-7.18 (m, 9H, Ar—H), 8.89 (s, 2H, Ar—OH), 9.53 (s, 1H, Ar—OH), $^{13}$C NMR (DMSO) δ 14.0 (Ar—O(CH$_2$)$_5$CH$_3$), 22.3 (Ar—CH$_2$—COOH), 24.8 (Ar—O(CH$_2$)$_4$CH$_2$CH$_3$), 29.3 (Ar—O(CH$_2$)$_3$CH$_2$CH$_2$CH$_3$), 29.7 (Ar—O(CH$_2$)$_2$CH$_2$(CH$_2$)$_2$CH$_3$), 30.3 (Ar—OCH$_2$CH$_2$(CH$_2$)$_3$CH$_3$), 30.6 and 31.7 (Ar—CH$_2$—Ar), 77.2 (Ar—OCH$_2$(CH$_2$)$_4$CH$_3$), 123.2; 124.2; 125.4; 126.9; 127.9; 129.6; 134.0 (Ar), 147.8 and 150.0 (ArC—OH), 151.9 (ArC—O(CH$_2$)$_5$CH$_3$).

ES mass spectrum m/z: 683.1 [M+H]+, 681.5 [M–H]−.

Example 6

Synthesis of 5,11,17 tris-[(carboxylato)methyl]25-mono-dodecyl 26,27,28 tris-hydroxycalix[4]arene—compound 5d 5 g of tris-[(cyano)methyl]monododecyloxy26,27,28 tris-hydroxycalix-[4]arene in 50 ml of EtOH are placed in a flask. 50 ml of 3M KOH are added. The reaction mixture is heated under reflux for 72 hrs. The solution is cooled, treated with 500 ml of iced water, and acidified with a 12M solution of HCl.

The yellow product is recovered by filtration then brought to reflux for 72 hrs in 50 ml of MeOH and 4.5 g of NaOH in 50 ml of water. The solution is cooled, treated with 250 ml of iced water, acidified with HCl, filtered and washed with water to yield the 5,11,17 tris-[(carboxy)methyl]25-mono-dodecyloxycalix[4]arene in the form of a yellow solid in a yield of 71%, M.Pt.=210° C., $^1$H NMR (DMSO) δ 0.81 (t, 3H, $^2J_{H-H}$=7.0 Hz, Ar—O(CH$_2$)$_{11}$CH$_3$), 1.01 (m, 4H, Ar—O(CH$_2$)$_9$CH$_2$CH$_2$CH$_3$), 1.03 (m, 4H, Ar—O(CH$_2$)$_7$CH$_2$CH$_2$(CH$_2$)$_2$CH$_3$), 1.10 (m, 4H, Ar—O(CH$_2$)$_5$CH$_2$CH$_2$(CH$_2$)$_4$CH$_3$), 1.25 (m, 2H, Ar—O(CH$_2$)$_4$CH$_2$CH$_2$(CH$_2$)$_5$CH$_3$), 1.44 (m, 2H, Ar—O(CH$_2$)$_3$CH$_2$CH$_2$(CH$_2$)$_6$CH$_3$), 1.67 (m, 2H, Ar—O(CH$_2$)$_2$CH$_2$CH$_2$(CH$_2$)$_7$CH$_3$), 2.01 (m, 2H, Ar—OCH$_2$CH$_2$CH$_2$(CH$_2$)$_8$CH$_3$), 3.18 (s, 2H, Ar—CH$_2$—COOH), 3.30 (s, 4H, Ar—CH$_2$—COOH), 3.35 (d, 2H, $^2J_{H-H}$=13.2 Hz, Ar—CH$_2$—Ar), 3.47 (d, 2H, $^2J_{H-H}$=13.2 Hz, Ar—CH$_2$—Ar), 4.01 (t, 2H, 2JH—H=7.1 Hz, Ar—OCH$_2$(CH$_2$)$_{10}$CH$_3$), 4.13 (d, 2H, $^2J_{H-H}$=13.2 Hz, Ar—CH$_2$—Ar), 4.17 (d, 2H, $^2J_{H-H}$=13.2 Hz, Ar—CH$_2$—Ar), 6.83-7.12 (m, 9H, Ar—H), 8.91 (s, 2H, Ar—OH), 9.53 (s, 1H, Ar—OH), $^{13}$C NMR (DMSO) δ 13.8 (Ar—O(CH$_2$)$_{11}$CH$_3$), 21.2 (Ar—CH$_2$—COOH), 24.6 (Ar—O(CH$_2$)$_{10}$CH$_2$CH$_3$), 24.8 (Ar—O(CH$_2$)$_9$CH$_2$CH$_2$CH$_3$), 28.7 (Ar—O(CH$_2$)$_8$CH$_2$(CH$_2$)$_2$CH$_3$), 28.8 (Ar—O(CH$_2$)$_7$CH$_2$(CH$_2$)$_3$CH$_3$), 29.1 (Ar—O(CH$_2$)$_6$CH$_2$(CH$_2$)$_4$CH$_3$), 29.4 (Ar—O(CH$_2$)$_5$CH$_2$(CH$_2$)$_5$CH$_3$), 29.6 (Ar—O(CH$_2$)$_4$CH$_2$(CH$_2$)$_6$CH$_3$), 29.8 (Ar—O(CH$_2$)$_3$CH$_2$(CH$_2$)$_7$CH$_3$), 29.9 (Ar—O(CH$_2$)$_2$CH$_2$(CH$_2$)$_8$CH$_3$), 30.2 (Ar—OCH$_2$CH$_2$(CH$_2$)$_9$CH$_3$), 30.5 and 31.6 (Ar—CH$_2$—Ar), 77.8 (Ar—OCH$_2$(CH$_2$)$_{10}$CH$_3$), 123.1; 124.3; 124.6; 127.2; 128.4; 129.7; 134.1 (Ar), 147.1 and 150.3 (ArC—OH), 151.4 (ArC—O(CH$_2$)$_{11}$CH$_3$), 170.3 (Ar—CH$_2$—COOH).

ES mass spectrum m/z: 767.2 [M+H]+, 765.1 [M–H]−.

Example 7

Surfactant Properties—1

Figure 1:
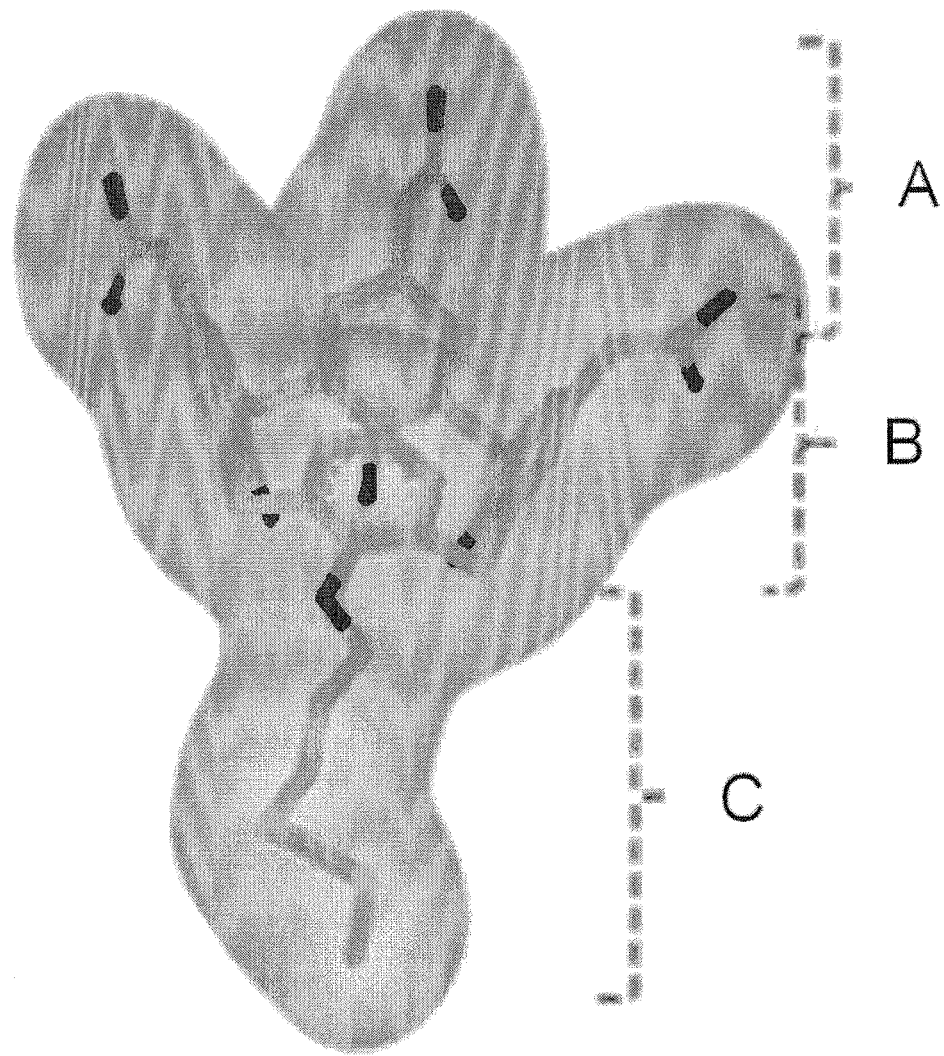
Figure 2:
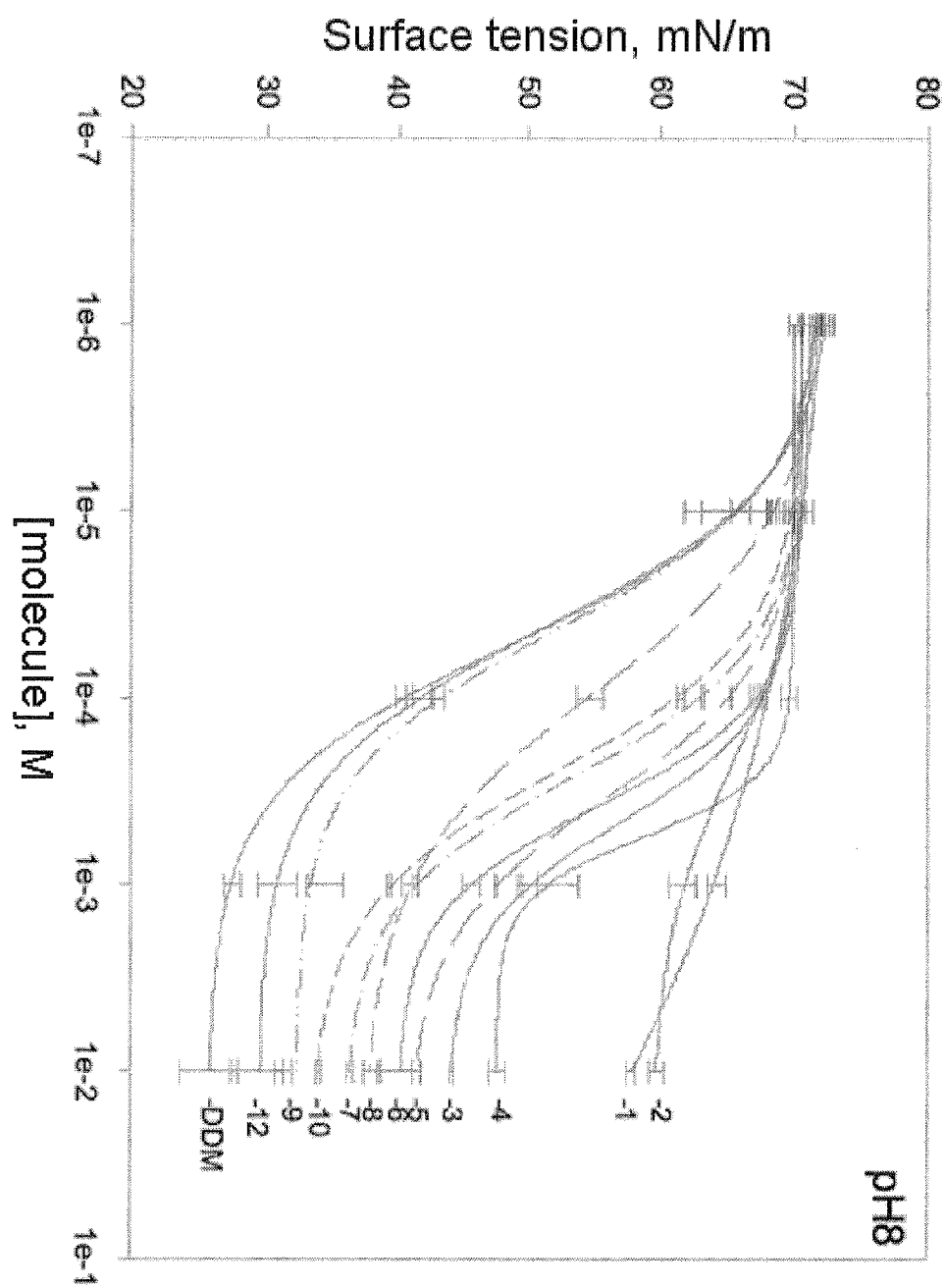

FIG. 2 shows the surfactant effect of the p(COOH)$_3$—Ar4-o(C$_n$H$_{2n+1}$) molecules, n=1-12 carbon atoms. As shown, the ability to decrease the surface tension of water, an effect typical of a surfactant, increases with the number of carbon atoms on the aliphatic chain. The molecules of calixarene having a shorter aliphatic chain do not modify the surface tension of water much, which signifies that their detergent properties are limited. On the other hand, molecules containing a longer alkyl chain (n=3 to 12) behave like detergents.

As expected, the potential of the surfactant increases with the length of the alkyl chain, and the molecule p(COOH)$_3$—Ar4-o(C$_{12}$H$_{25}$) shows surfactant properties close to those of DDM (β-D-dodecyl malto-pyranoside), a nonionic detergent typically used for solubilizing the membrane of proteins.

This example illustrates the first property of the calixarene compounds of the invention, namely that the p(COOH)$_3$—Ar4-o(C$_n$H$_{2n+1}$) calixarenes, n=3-12 behave like surfactants.

Figure 3:
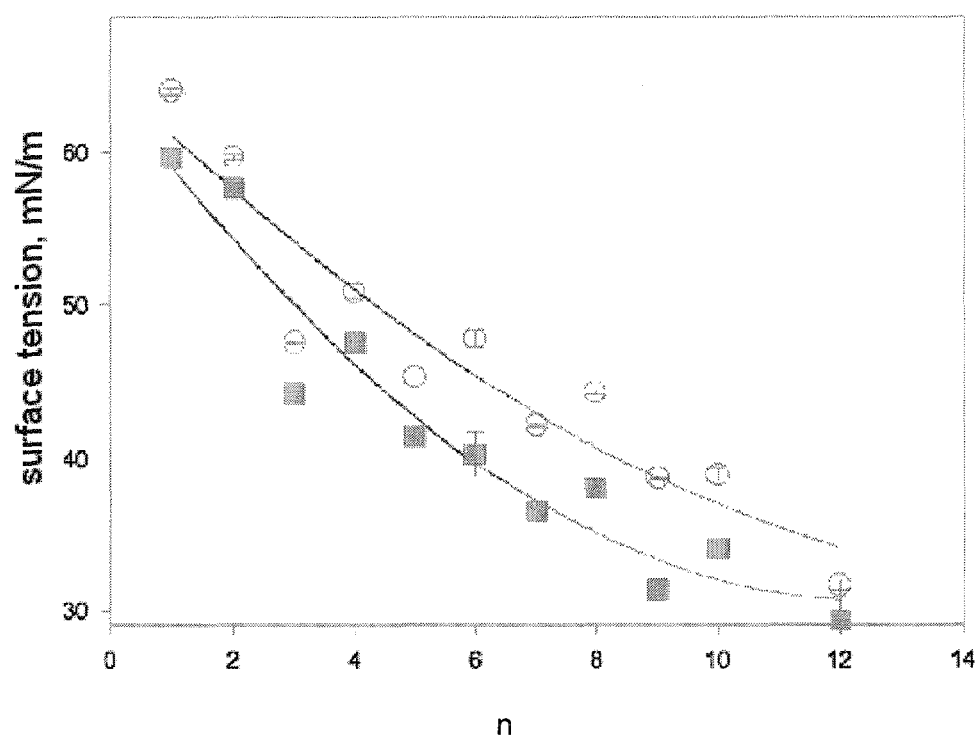

As shown in FIG. 3, the pH modulates the potential of the molecules on the surface tension. At pH 6 and 8, the surface tension increases regularly with the length of the alkyl chains reaching a plateau which corresponds to half the initial surface tension (n=12 at pH 8.0).

These effects illustrate a property of the invention which is that simply changing the pH makes it possible to modulate the surface tension of the medium in the presence of the calixarenes of the invention. This effect can be reduced or amplified depending on the length of the alkyl chain of the calixarenes of the invention.

Example 8

Surfactant Properties—2

Figure 4:
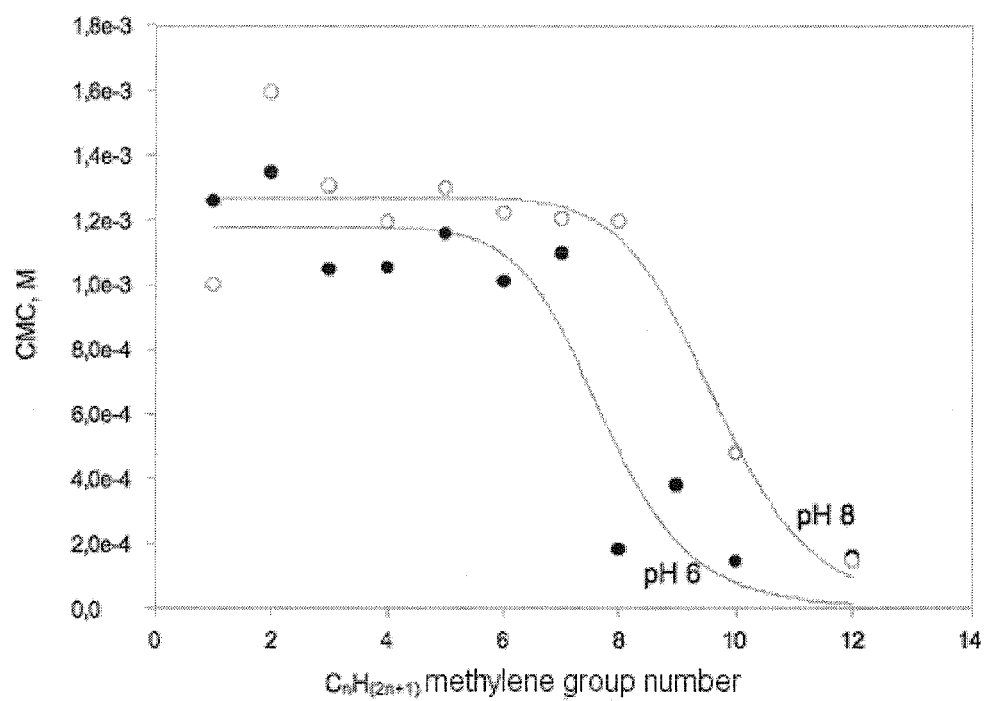

As shown in FIG. 4, the p(COOH)$_3$—Ar4-o(C$_n$H$_{2n+1}$) calixarenes, n=1-12 behave like detergents with a Critical Micellar Concentration (CMC) which can range from 0.15 to 1.5 mM. Critical Micellar Concentration (CMC) is understood to mean the concentration beyond which the concentration of the detergent molecules no longer increases since said molecules are involved in micelles (FIG. 13). The molecules containing an alkyl chain with a number of methylene groups lower than 8 exhibit a CMC of the mM order which does not depend on the pH. Conversely, when the alkyl chains include more than 8 methylene groups, the resulting CMC decreases appreciably to 0.15 mM when the pH increases from 6 to 8.

This example illustrates an important property of the calixarenes of the p(COOH)$_3$—Ar4-o(C$_n$H$_{2n+1}$) series, n=1-12 whose sensitivity to the pH depends on the length of the alkyl chain. This property is particularly marked for the p(COOH)$_3$—Ar4-o(C$_n$H$_{2n+1}$), n=9-12 calixarenes which can be used either at acidic pH or at basic pH, to encourage or discourage the formation of micelles. This property is typically to facilitate the removal of the detergent without increasing its concentration during the stage of concentration of the membrane of the solubilized protein.

Example 9

Interaction of p(COOH)$_3$—Ar4-o(C$_n$H$_{2n+1}$) with Amino Acids

Figure 5:
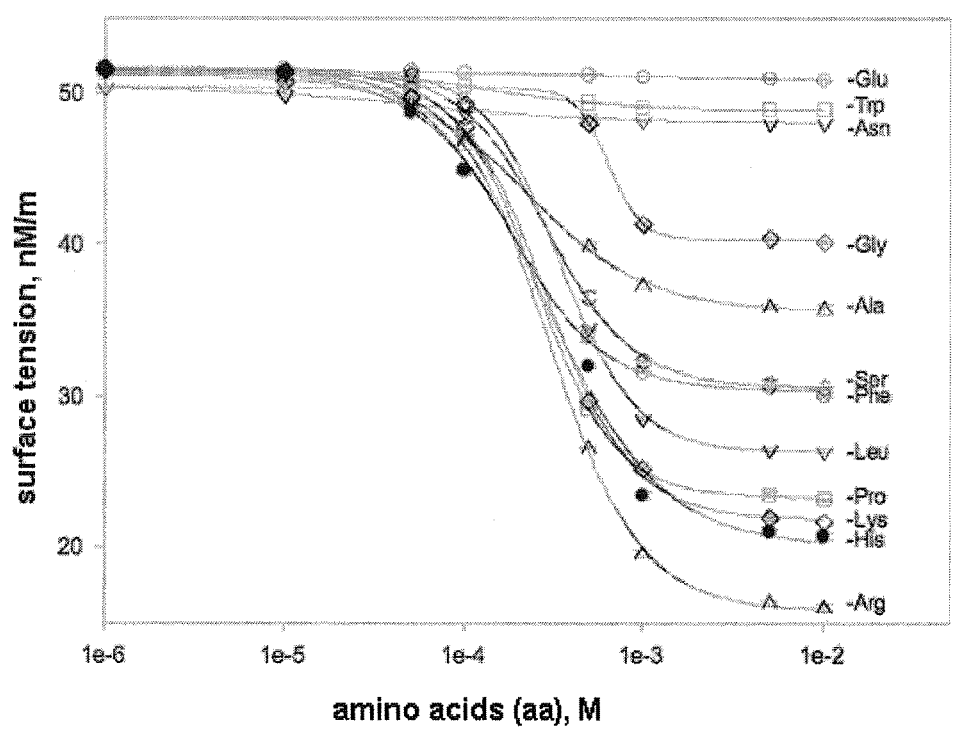

FIG. 5 illustrates the unique property of the calixarenes of the p(COOH)$_3$—Ar4-o(C$_n$H$_{2n+1}$) series, exemplified with n=7, of forming complexes with amino acids, modulating the surface tension of the medium. No effect is observed with amino acids such as glutamic acid, or its amino derivative, asparagine. A moderate effect is observed with glycine. This effect is amplified with hydrophobicity (alanine, phenylalanine, leucine) and becomes very pronounced with the positively charged amino acids such as histidine, lysine and arginine.

This example illustrates an important property of the molecule p(COOH)$_3$—Ar4-o(C$_7$H$_{15}$) (and others), with which the surfactant potential can be easily increased by adding positively charged amino acids. The resulting complexes are close to zwitterionic compounds.

Example 10

Size of Aggregates

Table 1 shows the aggregation state of the p(COOH)$_3$—Ar4-o(C$_n$H$_{2n+1}$) molecules.

TABLE 1

Aggregation state of p(COOH)$_3$—Ar4—o(C$_n$H$_{2n+1}$) molecules
Apparent diameter (nm)

| Compound | pH 2 | pH 4 | pH 6 | pH 8 |
|---|---|---|---|---|
| 5a | 950 | 340 | 22 | 270 |
|    |     |     | 260 |     |
| 5b | 500 | 550 | 145 | 270 |
|    |     | 90  |     | 25  |
| 5c | 850 | 210 | 400 | 210 |
|    |     | 890 |     | 6   |
| 5d | 880 | 100 | 190 | 730 |
|    |     | 40  |     | 8   |

As illustrated in table 1, all the systems observed form aggregates of the micellar type.
The Biological Effects of the p(COOH)$_3$—Ar4-o(C$_n$H$_{2n+1}$) Molecules The p(COOH)$_3$—Ar4-o(C$_n$H$_{2n+1}$) series were subjected to tests on the solubilization of BmrA, a membrane protein of the ABC transporter family and which protects the cells against the efflux and the leakage of xenobiotics towards the exterior of the cell [Chami 2002 JMB 315 1075; Orelle 2003 JBC 278-47 47002].

Figure 6:
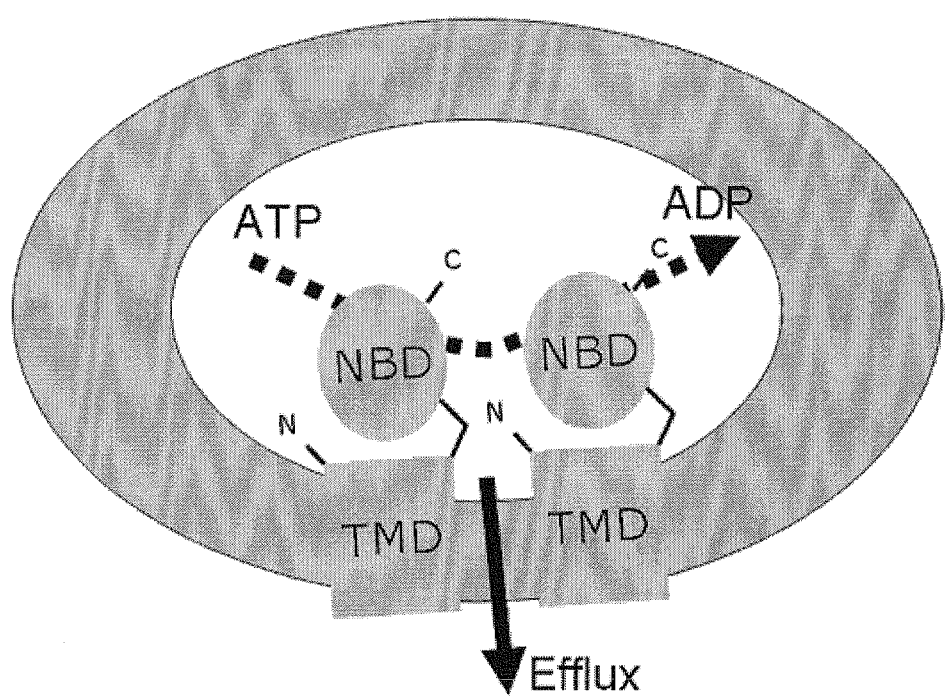

As shown diagrammatically in FIG. 6, BmrA is a homodimeric protein inserted in the plasma membrane of the bacterium. This protein expels xenobiotics via the hydrolysis of ATP, an enzymatic activity which depends on the correct folding of the transporter and which requires lipids [7]. Such activity is used to verify the functional integrity of the protein in the course of the solubilization procedure.

Example 11

Biological Membrane Solubilization Capacity of the Calixarenes of the Invention The competent bacteria C41 BL21(DE3) *E. coli* (*Escherichia coli*) were transformed with the plasmid pET15b-BMRA bearing the gene coding for BmrA and placed under the control of an inducible promoter and a gene coding for the protein conferring resistance to ampicillin. A positive clone was cultured in a liquid medium at 37° C. and 200 rpm in the presence of ampicillin until a semi-exponential growth phase. The expression of BmrA is induced by addition of 1 mM of isopropyl thio β-galactoside and continued at 25° C. for 4 hrs. The bacteria were harvested by centrifugation, disrupted in a French press, and the membrane fraction was isolated by a series of centrifugation stages at low and high speeds. The protein content was evaluated by colorimetry [8] and set at 20 mg/ml (20 mM Tris-Cl pH 8.0, 200 ml NaCl, 300 mM sucrose) before freezing and storage in liquid nitrogen. Before use, the membrane fraction is then rapidly thawed in water and maintained at 4° C. in ice.

The solubilization is effected at 4° C. (or at ambient temperature –23° C.—when indicated, by diluting the membrane fraction in the same buffer to a final concentration of 2 mg proteins/ml, then adding the detergents and the molecules being tested at 10 mg/ml (1%) or less when indicated, followed by an incubation of 2 hrs at 4° C. The solubilized or non-solubilized protein fractions are separated by a 200,000×g centrifugation stage for 1 hr at 10° C. Each centrifugation plug is suspended in the initial volume and loaded, together with the supernatant onto an electrophoresis of the Laemmli gel polyacrylamide type (SDS PAGE) [9] and as described for example in [7] to analyze their proteins content. Under such conditions, BmrA migrates at about 70,000 daltons.

The ATPase activity is measured by evaluating the inorganic phosphate content (Pi) after 5 minutes of incubation at 37° C. The fraction of Pi produced by other ATPase activities is deducted by measuring the same activity in the presence of 1 mM of ortho vanadate which inhibits the ATPase activity of BmrA (for example as described in [10]).

Figure 7:
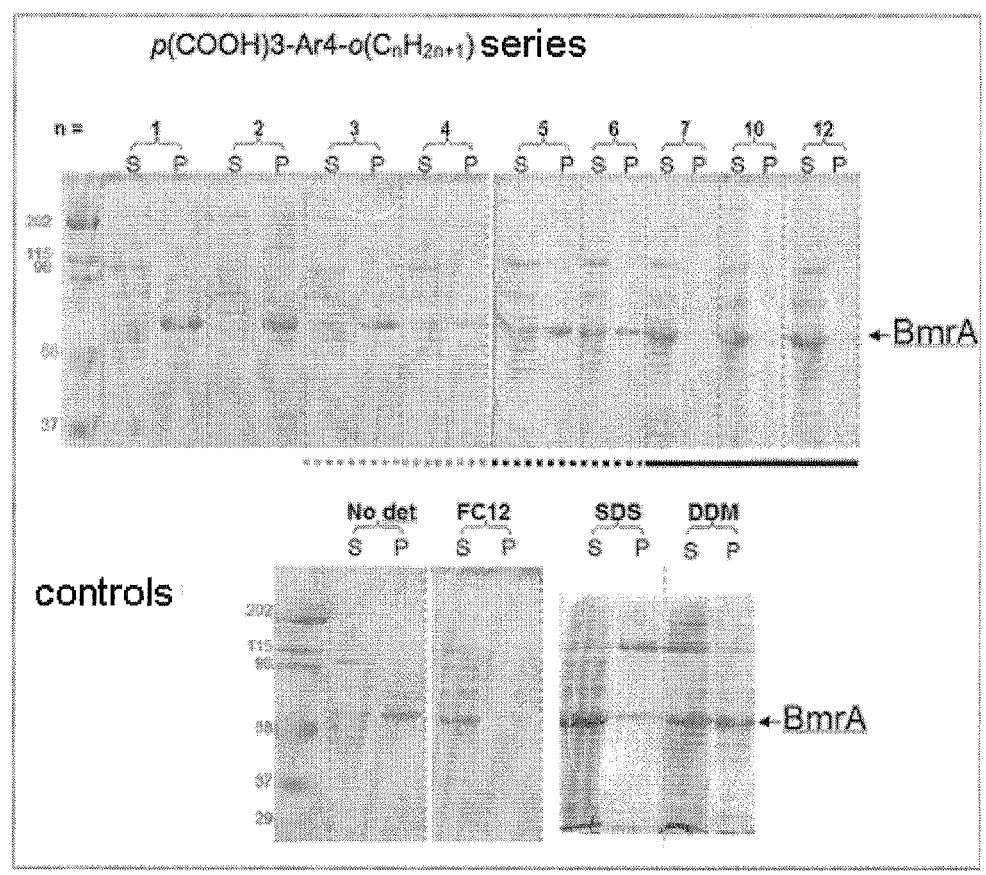

As shown in FIG. 7, BmrA is increasingly found in the supernatant, as a function of the length of the alkyl chain of the $p(COOH)_3$—Ar4-o($C_nH_{2n+1}$) molecules. No solubilization takes place with the shortest molecules (n=1 or 2) giving a diagram comparable to that obtained with no detergent ("no det" lines). The solubilization increases progressively with n=3 or 4, and is more pronounced with n=5 and 6 leading to the same diagram as that obtained with DDM. The solubilization appears complete for n≧7, as obtained with FC12 or SDS. Consequently, these molecules efficiently solubilize the membrane proteins.

Figure 8:
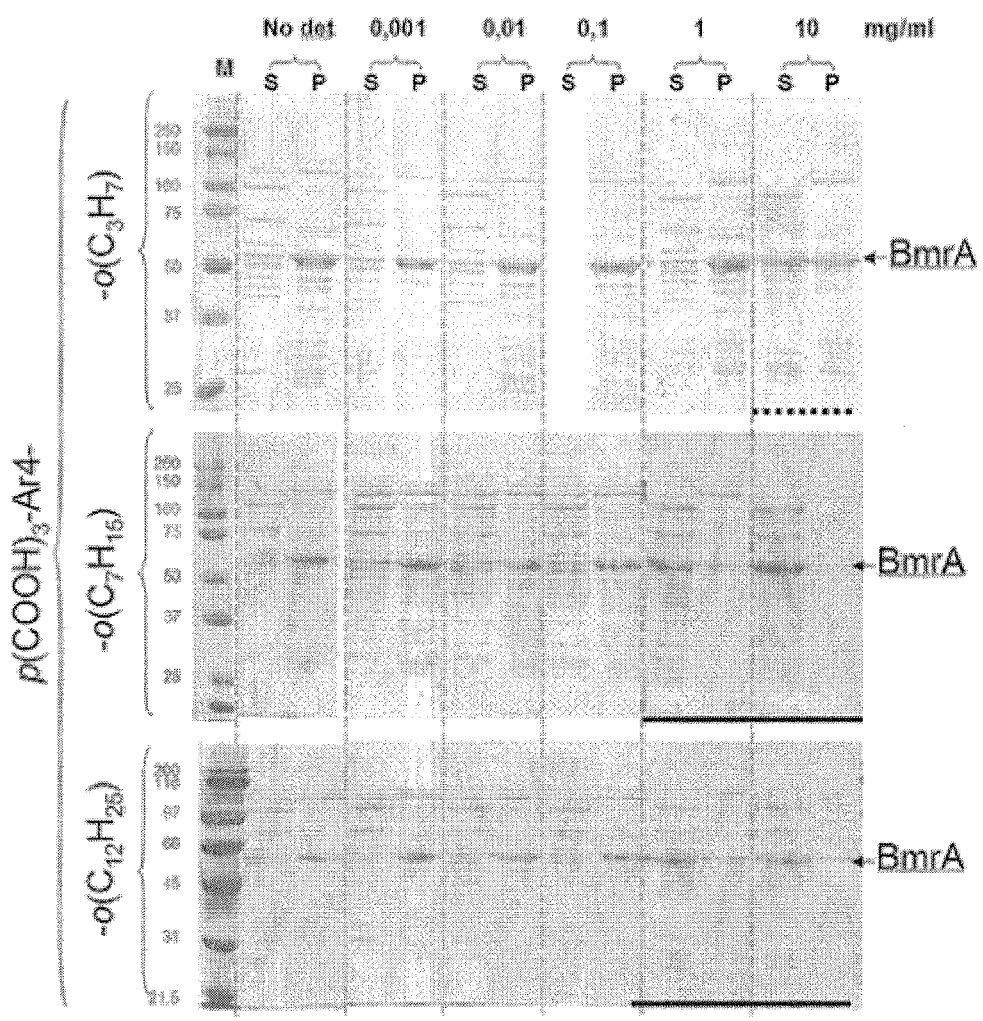

This is confirmed with the data from FIG. 8, which show that the solubilization takes place at a concentration of molecules ≧CMC, about 1.5 mM for the heptyl compound (1 g/L=1.6 mg/ml) whereas this is not the case for the dodecyl compound, given that at a CMC of 0.15 mM (corresponding to 0.1 g/L), no solubilization takes place, probably because of an excessively low detergent/protein ratio.

Table 2 indicates the g/L correspondence in M for the molecules tested.

chain) and control detergents (FC12 and C12E, an uncharged detergent) on the ATPase activity before, during and after solubilization of BmrA. As typically observed, the ATPase activity decreases with the solubilization as observed for FC12 and $C_{12}E_8$.

Figure 9:
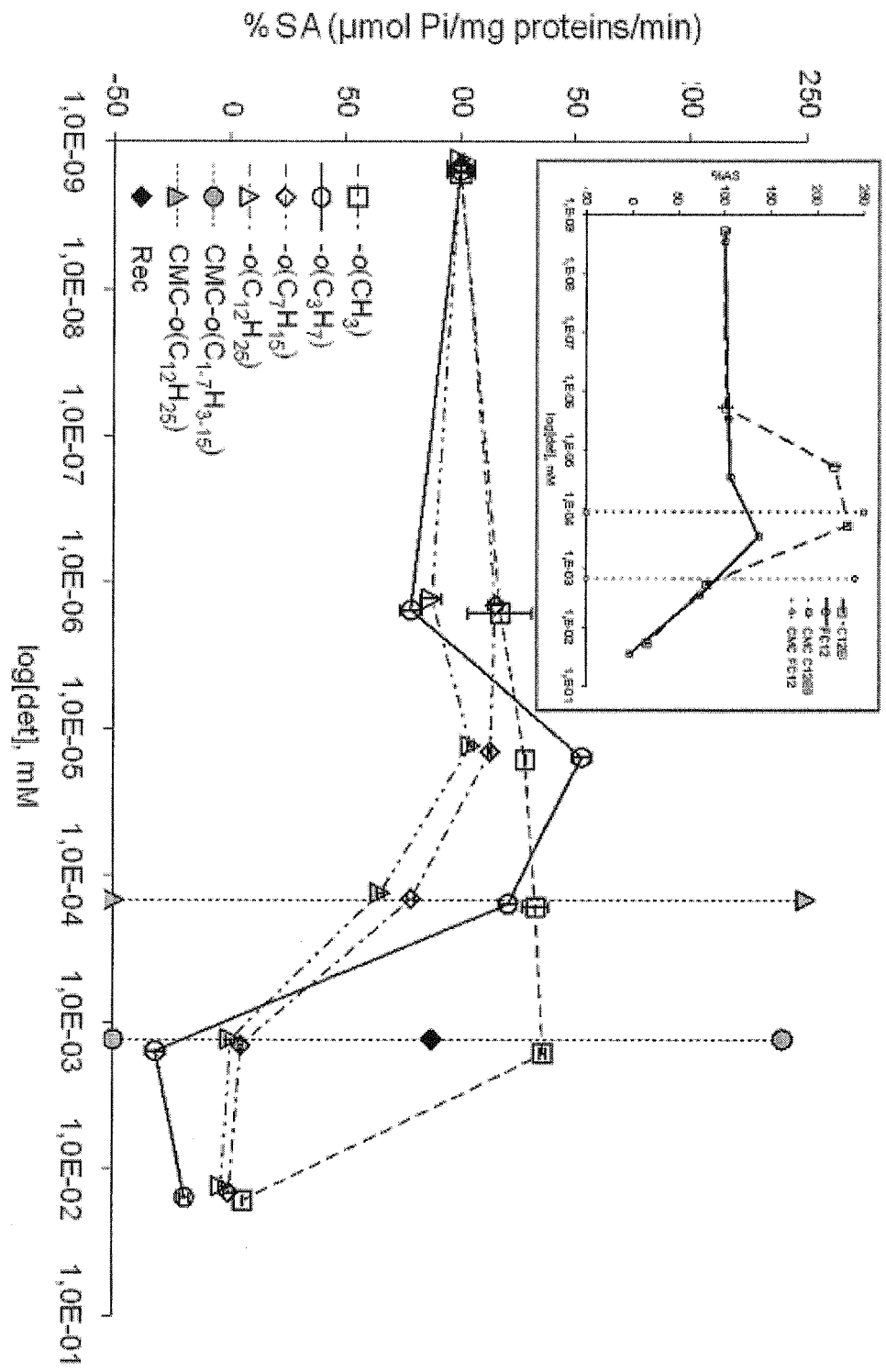

Remarkably, the comparison between FIGS. 8 and 9 shows that the heptyl molecule, at 1 mg/ml, solubilizes BmrA rather effectively, whereas that concentration, slightly lower than the CMC, does not lead to inactivation. This is likewise true for the dodecyl compound, at the same concentration, 1 mg/ml, 1/10 of CMC.

The experiments on reconstitution of BmrA in lipid bilayers after removal of the detergent show a totally recovered ATPase activity (black lozenge in FIG. 9) indicating that the molecules of the invention preserve the topology of BmrA in a functional state.

Example 13

Figure 10:
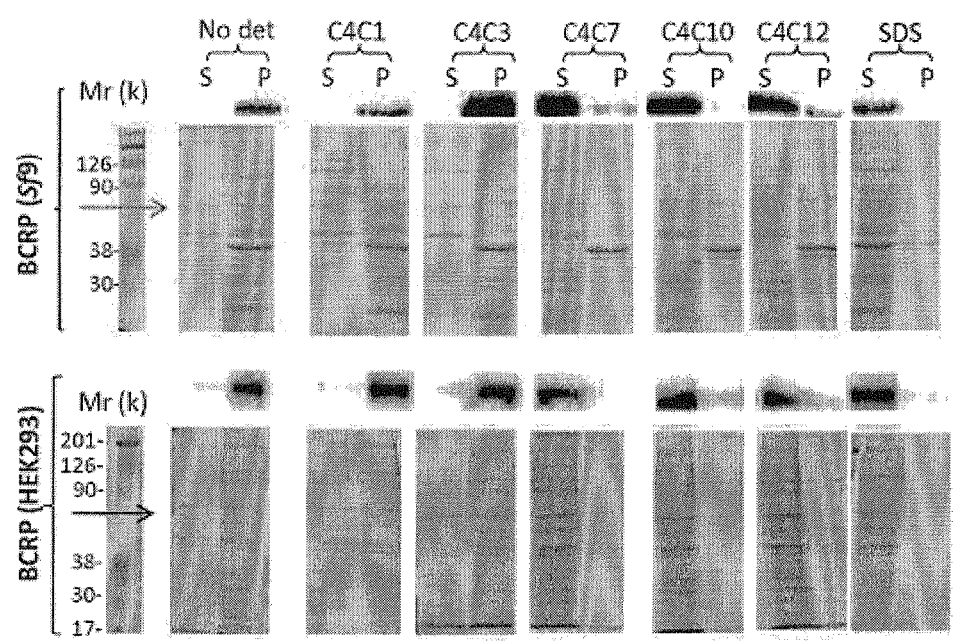
FIG. 10 shows the extraction of the BCRP protein (to be defined) from i) Sf9 insect cells (at top of diagram) and ii) HEK293 human cells (at bottom of diagram). This shows the ability of the calixarenes used to extract the membrane proteins of different cell lines.

Extraction of the BCRP Protein of Human Origin According to the Method of the Invention The BCRP protein, derived from a human gene, was expressed in HEK293 human cells or in Sf9 insect cells into which the corresponding gene was transfected. This protein was likewise efficiently solubilized with the calixarene derivatives of formula (I) containing heptyl or longer chains, as is shown by FIG. 10.

These experiments show that the method according to the invention using trianionic calix[4]arenes is an effective method for the extraction of a given membrane protein, depending on the choice of calixarene from the homologous series which either enriches the supernatant, or leaves the protein in the plug. This extraction can possibly be followed by a purification stage.

Example 14

Effect of the Solubilization by the Calixarenes According to the Invention on the Enzymatic Activity of ABC Transporters The proteins of the ABC transporter family are very sensitive to solubilization, this stage often impairing their

TABLE 2

Molecular weights (MW), critical micellar concentrations (CMC) and correspondence between the mass and the molar concentrations of the molecules tested

| | | | [compounds], M | | | | |
|---|---|---|---|---|---|---|---|
| $p(COOH)_3$—Ar4— | MW | CMC, M | 10 g/L | 1 g/L | 0.1 g/L | 0.01 g/L | 0.001 g/L |
| $o(C_1H_3)$ | 612 | >1.5E−03 | 1.6E−02 | 1.6E−03 | 1.6E−04 | 1.6E−05 | 1.6E−06 |
| $o(C_3H_7)$ | 640 | ~1.5E−03 | 1.6E−02 | 1.6E−03 | 1.6E−04 | 1.6E−05 | 1.6E−06 |
| $o(C_7H_{15})$ | 696 | ~1.5E−03 | 1.4E−02 | 1.4E−03 | 1.4E−04 | 1.4E−05 | 1.4E−06 |
| $o(C_{12}H_{25})$ | 766 | ~1.5E−04 | 1.3E−02 | 1.3E−03 | 1.3E−04 | 1.3E−05 | 1.3E−06 |

Example 12

Effect of Solubilization by the $p(COOH)_3$—Ar4-o ($C_nH_{2n+1}$) Series on the ATPase Activity of BmrA The effect of the solubilization by the $p(COOH)_3$—Ar4-o ($C_nH_{2n+1}$) series on the ATPase activity of BmrA was analyzed under the same conditions as in FIG. 8.

FIG. 9 shows the effect of the detergents used (calixarenes containing a methyl, propyl, heptyl or dodecyl aliphatic ATPase activity, at least reversibly. This impairment results from an absence of coupling between the NBD domains (nucleotide-binding domain) and TMDs (transmembrane domain).

The effects of the solubilization on the activity of the BmrA protein were evaluated with various C4Cn calixarenes, in other words the $p(COOH)_3$—Ar4-o($C_nH_{2n+1}$) calixarenes, but also with the control detergents such as Foscholine 12 (FC12) and β-D-dodecyl maltopyranoside (DDM), then the extracts obtained (supernatant fractions) were dialyzed in the presence of liposomes in order to restore a membrane environment, which enables the recovery of the activity of the protein.

Figure 11:
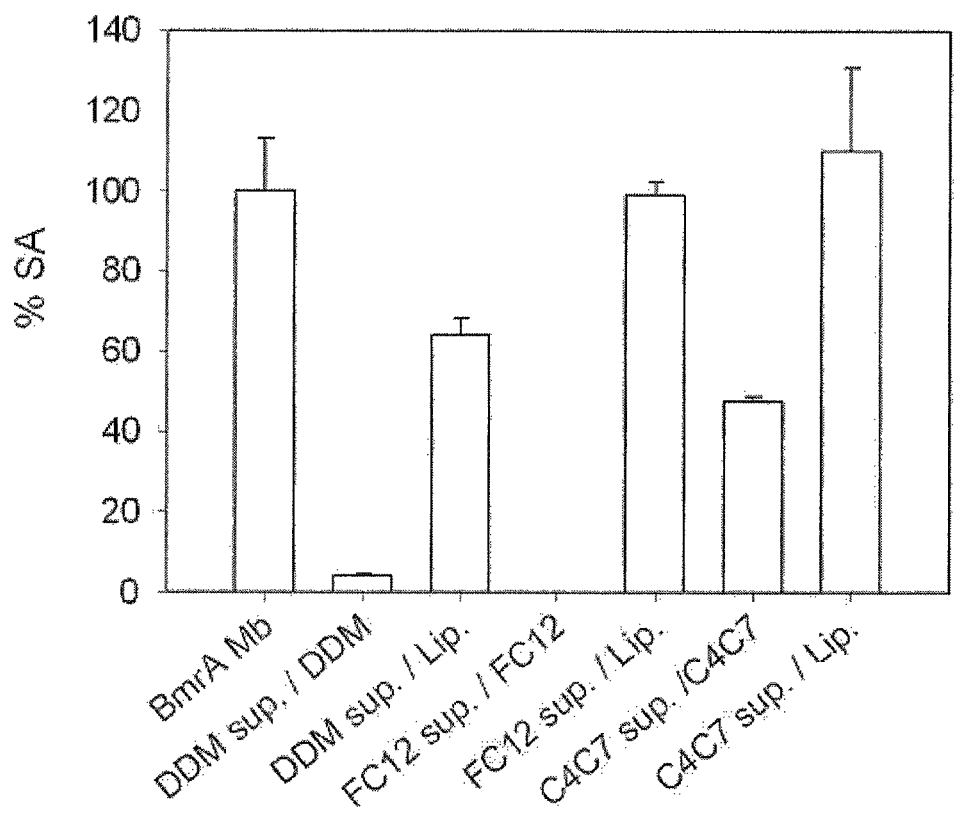
FIG. 11 shows the activity of the protein BmrA after extraction with different detergents, including β-D-dodecyl maltopyranoside (DDM), Foscholine 12 (FC12) and calix[4]arene-O-heptyloxy (C4C7). The percentage of specific ATPase activity sensitive to vanadate (% SA or % $VO_4$ sensitive Specific ATPase Activity) is evaluated for the following different cases.

The results shown in FIG. 11 show that once solubilized in the presence of DDM or FC12, the BmrA protein lost respectively 95 and 99% of its ATPase activity ("DDM Sup./DDM" and "FC12 Sup./FC12" columns respectively), relative to the BmrA activity which can be measured in these natural membranes ("BmrA Mb"). Nonetheless, this ATPase activity is recovered after removal of the detergents and reconstitution in the liposomes (FIG. 11, "DDM Sup./Lip." and "FC12 Sup./Lip." columns). When the C4C3 and C4C7 calixarene derivatives are used successively (see example 15), about 50% of the ATPase activity is preserved, demonstrating that these calixarene detergents make it possible to maintain the membrane protein in solution in a more rigid manner, unlike the detergents DDM and FC12. In fact, the rigid cone structure of the calixarenes of formula (I) enables the formation of rigid micelles which for the proteins constitute a medium comparable to the membrane environment, enabling better conservation of their three-dimensional structure and hence of their activity.

Example 15

Extraction and Purification of Proteins of the ABC Transporter Family with Calixarenes of Formula (I)

The advantage of the differential extraction of the BmrA protein by successively using the C4C3 then C4C7 calixarenes made it possible to enrich the supernatant fraction (as shown in FIG. 12A), before a subsequent purification by chromatography (FIGS. 12B-E).

The supernatant from C4C7 (sample "C4C7 S" in FIG. 12A) was subjected to nickel-affinity chromatography (FIGS. 12B and 12C), the BmrA protein bearing a hexahistidine tag at its N-terminal end. The protein thus combines with the resin and is eluted with imidazole in the presence of 0.3M NaCl making it possible to prevent the chelation of the nickel by the trianionic calixarene.

The same supernatant was also subjected to gel filtration chromatography in the presence of Foscholine 12 (FIG. 12D) in order to verify the oligomerization state of the transporter. BmrA was eluted at a volume of 12 mL, corresponding to an apparent molecular weight of 200,000 Da, which is a value compatible with a dimeric form of BmrA (2×65,000 Da) and a micelle of FC12 (70,000 Da). During this stage, the C4C7 calixarene was exchanged with FC12 and eluted between 15 and 25 mL, according to the UV detection (OD at 280 nm in milli-absorbance units mAU) and on SDS-PAGE (inset in FIG. 12D). The BmrA fraction (represented by a star in FIG. 12D) is recovered active (fraction a in FIG. 12E) in spite of the presence of FC12, which suggests that a functional structure of BmrA is preserved after solubilization with C4C7, and/or traces of C4C7 remain bound to the protein. An elevated ATPase activity was recovered after reconstitution of BmrA in the liposomes (fraction b in FIG. 12E). These results demonstrate clearly that a membrane protein can be purified by using a pair of calixarenes of formula (I) and chromatography stages, preserving the functional integrity of the protein at each of the stages.

List of References

[1]. Juliano, R. L., and Ling, V. (1976) A surface glycoprotein modulating drug permeability in Chinese hamster ovary cell mutants, *Biochim Biophys Acta* 455, 152-162.
[2]. Cole, S. P., Bhardwaj, G., Gerlach, J. H., Mackie, J. E., Grant, C. E., Almquist, K. C., Stewart, A. J., Kurz, E. U., Duncan, A. M., and Deeley, R. G. (1992) Overexpression of a transporter gene in a multidrug-resistant human lung cancer cell line, *Science* 258, 1650-1654.
[3]. Litman, T., Brangi, M., Hudson, E., Fetsch, P., Abati, A., Ross, D. D., Miyake, K., Resau, J. H., and Bates, S. E. (2000) The multidrug-resistant phenotype associated with overexpression of the new ABC half-transporter, MXR (ABCG2), *J Cell Sci* 113 (Pt 11), 2011-2021.
[4]. Chami, M., Steinfels, E., Orelle, C., Jault, J. M., Di Pietro, A., Rigaud, J. L., and Marco, S. (2002) Three-dimensional structure by cryo-electron microscopy of YvcC, an homodimeric ATP-binding cassette transporter from *Bacillus subtilis*, *J Mol Biol* 315, 1075-1085.
[5]. Orelle, C., Dalmas, O., Gros, P., Di Pietro, A., and Jault, J. M. (2003) The conserved glutamate residue adjacent to the Walker-B motif is the catalytic base for ATP hydrolysis in the ATP-binding cassette transporter BmrA, *J. Biol. Chem.* 278, 47002-47008.
[6]. Lenoir, G., Menguy, T., Corre, F., Montigny, C., Pedersen, P. A., Thinès, D., le Maire, M., and Falson, P. (2002) Overproduction in yeast and rapid and efficient purification of the rabbit SERCA1a $Ca^{2+}$-ATPase, *Biochim. Biophys. Acta* 1560, 67-83.
[7]. Steinfels, E., Orelle, C., Fantino, J. R., Dalmas, O., Rigaud, J. L., Denizot, F., Di Pietro, A., and Jault, J. M. (2004) Characterization of YvcC (BmrA), a multidrug ABC transporter constitutively expressed in *Bacillus subtilis*, *Biochemistry* 43, 7491-7502.
[8]. Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D. C. (1985) Measurement of protein using bicinchoninic acid, *Anal. Biochem.* 150, 76-85.
[9]. Laemmli, U. K. (1970) Cleavage of structural proteins during the assembly of the head of bacteriophage T4, *Nature* 227, 680-685.
[10]. Decottignies, A., Grant, A. M., Nichols, J. W., de Wet, H., McIntosh, D. B., and Goffeau, A. (1998) ATPase and multidrug transport activities of the overexpressed yeast ABC protein Yor1p, *J. Biol. Chem.* 273, 12612-12622.

The invention claimed is:
1. A method for selectively extracting membrane proteins from biological membranes comprising contacting an aqueous solution of the membrane protein to be extracted with at least one calixarene of formula (I):

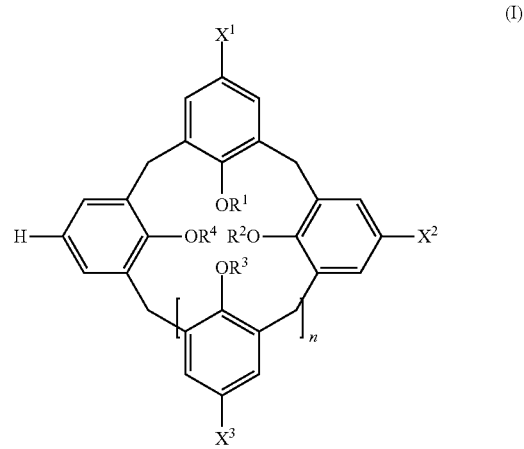

wherein:
n is a integer equal to 1;

R¹, R², R³ and R⁴ independently of one another represent a hydrogen atom, or a linear or branched ($C_{1-12}$) alkyl group; and X¹, X², and X³ independently of one another represent a group —$(CH_2)_m$—COOR' in which m is a integer ranging from 0 to 10, and R' represents a hydrogen atom; or one of the pharmaceutically acceptable salts thereof, thereby obtaining an aqueous solution of membrane proteins complexed with the calixarenes of formula (I).

2. The method according to claim 1, wherein the membrane protein to be complexed is present in a biological membrane fraction obtained from a prokaryotic or eukaryotic, healthy or impaired organism.

3. The method according to claim 1, wherein the membrane protein is a protein selected from the group comprising the transport proteins.

4. The method according to claim 3, wherein the transport protein is an ABC transporter selected from the group of the P glycoproteins (Pgp/ABCB1), MRPI/ABCC1, BCRP/ABCG2 and BmrA.

5. The method according to claim 1, wherein the stage of contacting an aqueous solution comprising the membrane protein to be complexed with at least one calixarene of formula (I) is effected at a pH ranging from 5.5 to 10.

6. The method according to claim 1, wherein the stage of contacting an aqueous solution comprising the membrane protein to be complexed with at least one calixarene of formula (I) is effected at a temperature ranging from 0 to 100° C.

7. The method according to claim 1, wherein the stage of contacting an aqueous solution comprising the membrane protein to be complexed with at least one calixarene of formula (I) is effected at a calixarene concentration ranging from $10^{-6}$ to $10^{-2}$ M.

8. The method according to claim 1, wherein the stage of contacting an aqueous solution comprising the membrane protein to be complexed with at least one calixarene of formula (I) is effected with calixarenes in solution or calixarenes in colloidal aggregates.

9. The method according to claim 8, wherein the colloidal aggregate is selected from the group of micelles, liposomes, and lipid nanoparticles.

10. The method according to claim 1, wherein contacting an aqueous solution comprising the membrane protein to be complexed with at least one calixarene of formula (I) is optionally effected in the presence of at least one co-solute selected from the group of:

i) organic and inorganic salts selected from the group of the pharmaceutically acceptable salts;

ii) small biologically active molecules selected from the group of the amino acids, vitamins, lipids, steroids, carbohydrates or metabolites;

iii) oligomeric biologically active molecules selected from the group of the peptides, oligonucleotides and oligosaccharides; and iv) polymeric biological molecules selected from the group of the proteins, polynucleotides and polysaccharides.

11. The method according to claim 1, wherein the contacting stage is preceded by a stage in which:

the membrane protein to be complexed, or the membrane fraction containing the membrane protein to be complexed, is solubilized in a buffer solution, and the calixarene of formula (I) is added at pH ranging from 5.5 to 10.

12. The method according to claim 1, wherein the proteins complexed with the calixarenes of formula (I) and the non-complexed proteins are separated by centrifugation.

* * * * *